(12) United States Patent
Bangera et al.

(10) Patent No.: US 8,815,163 B2
(45) Date of Patent: *Aug. 26, 2014

(54) MATERIAL, SYSTEM, AND METHOD THAT PROVIDE INDICATION OF A BREACH

(71) Applicant: Searete LLC, Bellevue, WA (US)

(72) Inventors: Mahalaxmi Gita Bangera, Renton, WA (US); Roderick A. Hyde, Redmond, WA (US); Muriel Y. Ishikawa, Livermore, CA (US); Edward K. Y. Jung, Bellevue, WA (US); Jordin T. Kare, Seattle, WA (US); Erez Lieberman Aiden, Cambridge, MA (US); Nathan P. Myhrvold, Medina, WA (US); Dennis J. Rivet, Chesapeake, VA (US); Michael A. Smith, Phoenix, AZ (US); Elizabeth A. Sweeney, Seattle, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/950,849

(22) Filed: Jul. 25, 2013

(65) Prior Publication Data

US 2013/0309137 A1 Nov. 21, 2013

Related U.S. Application Data

(63) Continuation of application No. 12/927,972, filed on Nov. 29, 2010, now Pat. No. 8,501,103.

(51) Int. Cl.
*G05B 9/00* (2006.01)

(52) U.S. Cl.
USPC .......................... 422/117; 422/119; 340/540

(58) Field of Classification Search
None
See application file for complete search history.

(56) References Cited

U.S. PATENT DOCUMENTS

| | | | |
|---|---|---|---|
| 4,234,907 A | 11/1980 | Daniel |
| 5,157,379 A | 10/1992 | Dennison |
| 5,335,373 A | 8/1994 | Dangman et al. |
| 5,430,434 A | 7/1995 | Lederer et al. |
| 5,448,177 A | 9/1995 | Thompson |
| 5,549,924 A | 8/1996 | Shlenker et al. |
| 5,567,932 A | 10/1996 | Staller et al. |
| 5,734,323 A | 3/1998 | Hermes et al. |
| 5,911,848 A | 6/1999 | Haber et al. |
| 5,976,881 A | 11/1999 | Klingner |
| 6,060,986 A | 5/2000 | Lederer |

(Continued)

OTHER PUBLICATIONS

Briand et al.; "Integration of MOX gas sensors on polyimide hotplates"; Sensors and Actuators B: Chemical; 2008; pp. 430-435; vol. 130, No. 1.

(Continued)

*Primary Examiner* — Eric M Blount

(57) ABSTRACT

A multilayer material is described herein that includes a flexible inner layer and a flexible outer layer configured to enclose at least one signaling layer, the at least one signaling layer including at least one chemical compound. The multilayer material including the chemical compound within the at least one signaling layer is configured to release a gas-phase chemical compound to signal to a detector indicating a breach of the multilayer material. A multilayer material, a system, an article of clothing, or a method is described herein.

54 Claims, 3 Drawing Sheets

(56) References Cited

U.S. PATENT DOCUMENTS

| | | |
|---|---|---|
| 6,323,577 B1 | 11/2001 | Inoue et al. |
| 6,347,408 B1 | 2/2002 | Yeh |
| 6,395,383 B1 | 5/2002 | Maples |
| 6,841,601 B2 | 1/2005 | Serpico et al. |
| 6,850,162 B2 * | 2/2005 | Cacioli et al. .............. 340/573.1 |
| 6,851,844 B2 | 2/2005 | Guy |
| 6,995,353 B2 | 2/2006 | Beinhocker |
| 7,225,476 B2 * | 6/2007 | Cerbini et al. .................... 2/457 |
| 7,630,591 B2 | 12/2009 | Allen et al. |
| 7,683,797 B2 | 3/2010 | Woodard et al. |
| 7,927,558 B2 | 4/2011 | Kirollos et al. |
| 7,993,606 B2 | 8/2011 | Trentacosta et al. |
| 8,323,577 B2 | 12/2012 | Kapur et al. |
| 2004/0037091 A1 | 2/2004 | Guy |
| 2007/0208395 A1 | 9/2007 | Leclerc et al. |
| 2008/0183053 A1 | 7/2008 | Borgos et al. |
| 2009/0050812 A1 | 2/2009 | Dunleavy et al. |
| 2009/0159445 A1 | 6/2009 | Krishna et al. |
| 2009/0159446 A1 | 6/2009 | Cui et al. |
| 2009/0159447 A1 * | 6/2009 | Cui et al. ...................... 204/431 |
| 2009/0264036 A1 | 10/2009 | Yano et al. |
| 2010/0251466 A1 | 10/2010 | Langley et al. |
| 2011/0210856 A1 | 9/2011 | Beinhocker |

OTHER PUBLICATIONS

Briand et al.; "Micro-hotplates on polyimide for sensors and actuators"; Sensors and Actuators A: Physical; 2008; pp. 317-324; vol. 132, No. 8.

Buhr et al.; "Analysis of volatile flavor compounds by Proton Transfer Reaction-Mass Spectrometry; fragmentation patterns and discrimination between isobaric and isomeric compounds"; International Journal of Mass Spectrometry; 2002; pp. 1-7; vol. 221.

Courbat et al.; "Evaluation of pH indicator-based colorimetric films for ammonia detection using optical waveguides"; Sensors and Actuators B: Chemical; 2009; pp. 62-70; vol. 143; Elsevier B.V.

Courbat et al.; "Thermal Simulation and Characterization for the Design of Ultra-Low Power Micro-Hotplates on Flexible Substrate"; IEEE Sensors; 2008 Conference; pp. 74-77; IEEE.

"Edmund Optics® Filter Capabilities"; Product Information; 6 pgs.; Edmund Optics Inc.; printed on Nov. 16, 2010; located at www.edmundoptics.com.

"E" Series long wavelength pass filters; 1998; product sheet; one page; located at www.gentexcorp.com.

"FOX-TEK announces smart material tests at NASA successful"; Fiber Optics Weekly Update; Apr. 22, 2005; one page; located at www.fox-tek.com.

IRC-A1 Carbon Dioxide Infrared Sensor; Technical Specification; pp. 1-3; located at www.alphasense.com; printed on Aug. 24, 2010.

IRC-TM NDIR $CO_2$ Transmitter PCB; Technical Specification; 1 pg.; located at www.alphasense.com; printed on Aug. 24, 2010.

Kim et al.; "Waterproof AlInGaP optoelectronics on stretchable substrates with applications in biomedicine and robotics"; Nature Materials; Nov. 2010; pp. 929-937; vol. 9; Macmillan Publishers Limited.

"Larry 2048 & 3000 Series Linear CCD Array Cameras/Detectors"; pp. 1-4; printed on Sep. 21, 2010; located at www.amesphotonics.com.

Lindinger et al.; Environmental, Food and Medical Applications of Proton-Transfer-Reaction Mass Spectrometry (PTR-MS); Advances in Gas-Phase Ion Chemistry; 2001; pp. 1-48; vol. 4; Elsevier Science B.V.

Measures et al.; "Structurally integrated fiber optic damage assessment system for composite materials"; Applied Optics; Jul. 1, 1989; pp. 2626-2633; vol. 28, No. 13; Optical Society of America.

Nyström et al.; "Ultrafast All-Polymer Paper-Based Batteries"; Nano Letters; 2009; pp. 3635-3639; vol. 9, No. 10; American Chemical Society.

Oprea et al.; "Capacitive Gas Sensor Arrays on Plastic Substrates for Low Power and Mobile Applications"; pp. 1431-1434; printed on Sep. 21, 2010.

Oprea et al.; "Integrated Temperature, Humidity and Gas Sensors on Flexible Substrates for Low-Power Applications"; IEEE Sensors; 2007 Conference; pp. 158-161; IEEE.

"Photomultiplier Tubes Basics and Applications"; Hamamatsu; Third Edition; 2008; Cover Page; Table of Contents and pp. 22-27; Hamamatsu Photonics K.K.

Polymer Optical Fiber Specification Sheet; 2007; 4 pgs.; Moritex USA Incorporated.

Potyrailo et al.; "Multianalyte Chemical Identification and Quantitation Using a Single Radio Frequency Identification Sensor"; Anal. Chem.; 2007; pp. 45-51; vol. 79, No. 1; American Chemical Society.

Qi et al.; "Piezoelectric Ribbons Printed onto Rubber for Flexible Energy Conversion"; Nano Letters; Jan. 26, 2010; pp. 524-528; American Chemical Society.

"Red enhanced Avalanche Photodiode"; Silicon Sensor Specification Sheet; Jan. 27, 2010; pp. 1-2; located at www.silicon-sensor.com.

"Sensitive Real-Time Trace Gas Detector"; product information; pp. 1-2; located at www.PTRMS.com/products; printed on Aug. 24, 2010.

"Si APD array S8550"; production information; Jun. 2006; pp. 1-2; Hamamatsu Photonics K.K.; located at www. hamamatsu.com.

Silicon Sensor PIN Photo Diode Data Sheet; Mar. 9, 2010; pp. 1-3; Silicon Sensor International AG; located at www.silicon-sensor.com.

Tennyson et al.; "Structural Health Monitoring 2005: Advancements and Challenges for Implementation", ed. Fuo-Kuo Chang; pp. 1621-1627, DEStech Publications, Inc., Lancaster, PA, Sep. 12, 2005.

"Ultraviolet (UV) Metal Can LED OUE8A Series"; OPTEK Technology Inc.; Jul. 2009; production information; pp. 1-8; located at www.optekinc.com.

* cited by examiner

MATERIAL, SYSTEM, AND METHOD THAT PROVIDE INDICATION OF A BREACH

PRIORITY APPLICATIONS

For purposes of the USPTO extra-statutory requirements, the present application constitutes a continuation of U.S. patent application Ser. No. 12/927,972, entitled MATERIAL, SYSTEM, AND METHOD THAT PROVIDE INDICATION OF A BREACH, naming Mahalaxmi Gita Bangera, Roderick A. Hyde, Muriel Y. Ishikawa, Edward K. Y. Jung, Jordin T. Kare, Erez Lieberman, Nathan P. Myhrvold, Dennis J. Rivet, Michael A. Smith, Elizabeth A. Sweeney and Lowell L. Wood, Jr. as inventors, filed 29 Nov. 2010.

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.

RELATED APPLICATIONS

U.S. patent application Ser. No. 12/927,968, entitled MATERIAL, SYSTEM, AND METHOD THAT PROVIDE INDICATION OF A BREACH, naming Mahalaxmi Gita Bangera, Roy P. Diaz, Roderick A. Hyde, Muriel Y. Ishikawa, Edward K. Y. Jung, Jordin T. Kare, Erez Lieberman, Nathan P. Myhrvold, Dennis J. Rivet, Michael A. Smith, Elizabeth A. Sweeney and Lowell L. Wood, Jr. as inventors, filed 29 Nov. 2010, is related to the present application.

U.S. patent application Ser. No. 13/135,369, entitled MATERIAL, SYSTEM, AND METHOD THAT PROVIDE INDICATION OF A BREACH, naming Mahalaxmi Gita Bangera, Roy P. Diaz, Roderick A. Hyde, Muriel Y. Ishikawa, Edward K. Y. Jung, Jordin T. Kare, Erez Lieberman, Nathan P. Myhrvold, Dennis J. Rivet, Michael A. Smith, Elizabeth A. Sweeney and Lowell L. Wood, Jr. as inventors, filed 30 Jun. 2011, is related to the present application.

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

A flexible multilayer material to be worn by a user is described herein that includes a protective, or impermeable or semi-permeable, barrier layer enclosing at least one signaling layer to signal a breach in the multilayer material. A detector is configured to detect a gas-phase chemical compound released from the at least one signaling layer following a breach of the multilayer material. The multilayer material is configured to release the gas-phase chemical compound from the at least one signaling layer to signal to the detector indicating a breach of the multilayer material. The signal from the detector is configured to notify and warn a wearer of the need to re-glove in the event that his or her multilayer material becomes torn or punctured with the result of exposing the wearer to a possibly hazardous material. In a clean room setting, a multilayer material can include at least one signaling layer including at least one chemical compound that can release a gas-phase chemical compound, wherein the gas-phase chemical compound can be detected by a detector indicating a breach of at least a portion of the multilayer material. The detector can be configured to notify or warn a clean room worker of a possible contamination of the clean room.

In some aspects, a multilayer material is described herein that includes a flexible inner layer and a flexible outer layer configured to enclose at least one signaling layer including at least one chemical compound; wherein the flexible outer layer is substantially impermeable to an environment and to the at least one chemical compound in the at least one signaling layer; and wherein the at least one chemical compound within the at least one signaling layer is configured to produce at least one gas-phase chemical compound configured to be released into the environment upon exposure of the at least one chemical compound to the environment. In an embodiment, an article of clothing can include the multilayer material.

The multilayer material can further include a detector configured to detect the at least one gas-phase chemical compound or a reaction product thereof in the environment indicating a breach of the multilayer material. The reaction product can be due to a reaction of the at least one gas-phase chemical compound and the environment. The gas-phase chemical compound can be due to a reaction of the at least one chemical compound and the environment. The detector can be configured to form a layer of the multilayer material. The detector can be configured to operate in contact with the multilayer material. The detector can be configured to measure one or more absolute levels of the at least one gas-phase chemical compound or the reaction product thereof. The detector can be configured to measure one or more comparisons between the one or more absolute levels and one or more baseline levels of the at least one gas-phase chemical compound or the reaction product thereof. The detector can be configured to measure the rate of change of concentration of the at least one gas-phase chemical compound or the reaction product thereof. The detector can be configured to identify the at least one gas-phase chemical compound or the reaction product thereof.

In some aspects, the at least one gas-phase chemical compound can be substantially removed from the environment within a specified time. The at least one gas-phase chemical compound can be substantially removed from the environment by a chemical reaction with at least one normal component of the atmosphere. The at least one gas-phase chemical compound can be substantially removed from the environment by a chemical reaction with a chemical released or exposed subsequent to detection of the at least one gas-phase chemical compound. The at least one gas-phase chemical compound can be substantially removed from the environment by condensation. The at least one gas-phase chemical compound can be substantially removed from the environment by photodissociation. The at least one gas-phase chemical compound can be substantially removed from the environment by active convection. The active convection can be continuous or is activated by detection of the at least one gas-phase chemical compound. The at least one gas-phase chemical compound can be substantially removed from the environment by passive convection. The at least one gas-phase chemical compound can be lighter or heavier than air in the environment.

The multilayer material can further include a remote receiver, wherein the detector is configured to deliver a signal to the remote receiver. The signal can include data associated with the identity of the at least one gas-phase chemical compound, concentration of the at least one gas-phase chemical compound, comparison of concentration of the at least one gas-phase chemical compound to baseline, or ratio of concentrations of the at least one gas-phase chemical compounds. The signal can include data associated with the identity of the reaction product, concentration of the reaction product, comparison of concentration of the reaction product to baseline, or ratio of concentrations of the reaction products. The signal can include a wireless signal. The detector can include at least one of a radio frequency identification sensor and a radio frequency identification reader. The multilayer material can include at least one of a radio frequency identification sensor and a radio frequency identification reader. The at least one signaling layer including the at least one chemical compound can include a liquid-phase chemical compound or a solid-phase chemical compound. The at least one signaling layer can include the at least one chemical compound includes the at least one gas-phase chemical compound. The at least one chemical compound can be microencapsulated in the at least one signaling layer. The at least one chemical compound can include, but is not limited to, mercaptan, carbon dioxide, 1-hexanol, sulfur hexafluoride, ethanethiol, or furaneol. The at least one chemical compound can include $^{13}CO_2$, $C^{18}O^{16}O$, $D_2O$, DHO, or other isotopically-distinctive compound. The at least one gas-phase chemical compound can be configured to be lighter or heavier than air and flow to the detector. The at least one gas-phase chemical compound can be transferred to the detector by active convection. The detector can be further configured to transmit metadata to the remote receiver. The metadata can include, but is not limited to, multilayer material identification, user identification, location of the breach in the multilayer material, detection event time, or multilayer material location. The detector can be configured to store signal data or metadata on board the detector for future readout. The detector or the remote receiver can be configured to communicate with a computing device. The computing device can be configured to activate a user interface configured to inform a wearer of the multilayer material, a co-worker, an individual, a manufacturer or a seller of the multilayer material, a supervisor, a safety official, or an insurance official.

The at least one signaling layer can include two or more chemical compounds in two or more different locations on the multilayer material, wherein the release of one or more gaseous chemical compounds derived from at least one of the two or more chemical compounds to the environment is configured to identify at least one release location on the multilayer material. The two or more different locations of the two or more chemical compounds in the at least one signaling layer can include one or more of two or more different lateral locations and two or more different layered locations on the multilayer material. In some aspects, each of the two or more different locations can have at least one distinct chemical compound. Each of the two or more different locations can have a distinct ratio of the two or more chemical compounds.

The multilayer material can include, but is not limited to, an article of clothing, a bandage, an enclosure, packaging, a surgical drape, a glove box, or a food wrapping. The at least one signaling layer can include two or more chemical compounds in a same location on the multilayer material, wherein the ratio of two or more gaseous chemical compounds derived from the two or more chemical compounds identifies the multilayer material or identifies the same location on the multilayer material.

In an embodiment, an article of clothing can include the multilayer material. An article of clothing is described herein that includes a multilayer material including a flexible inner layer and a flexible outer layer configured to enclose at least one signaling layer including at least one chemical compound; wherein the flexible outer layer is substantially impermeable to an environment and to the at least one chemical compound in the at least one signaling layer; and wherein the at least one chemical compound within the at least one signaling layer is configured to produce at least one gas-phase chemical compound configured to be released into the environment upon exposure of the at least one chemical compound to the environment. The at least one gas-phase chemical compound can be substantially removed from the environment within a specified time by various methods in order to lower the baseline levels of the gas-phase chemical compound for detection by the detector.

The article of clothing including the multilayer material can further include a detector configured to detect the at least one gas-phase chemical compound or a reaction product thereof in the environment indicating a breach of the multilayer material. The reaction product can be due to a reaction of the at least one gas-phase chemical compound and the environment. The gas-phase chemical compound can be due to a reaction of the at least one chemical compound and the environment. The detector can be configured to form a layer of the multilayer material. The detector can be configured to operate in contact with the multilayer material. The detector can be configured to measure one or more absolute levels of the at least one gas-phase chemical compound or the reaction product thereof. The detector can be configured to measure one or more comparisons between the one or more absolute levels and one or more baseline levels of the at least one gas-phase chemical compound or the reaction product thereof. The detector can be configured to measure the rate of change of concentration of the at least one gas-phase chemical compound or the reaction product thereof. The detector can be configured to identify the at least one gas-phase chemical compound or the reaction product thereof.

In some aspects, the at least one gas-phase chemical compound can be substantially removed from the environment within a specified time. The at least one gas-phase chemical compound can be substantially removed from the environment by a chemical reaction with at least one normal component of the atmosphere. The at least one gas-phase chemical compound can be substantially removed from the environment by a chemical reaction with a chemical released or exposed subsequent to detection of the at least one gas-phase chemical compound. The at least one gas-phase chemical compound can be substantially removed from the environment by condensation. The at least one gas-phase chemical compound can be substantially removed from the environment by photodissociation. The at least one gas-phase chemical compound can be substantially removed from the environment by active convection. The active convection can be continuous or is activated by detection of the at least one gas-phase chemical compound. The at least one gas-phase chemical compound can be substantially removed from the environment by passive convection. The at least one gas-phase chemical compound can be lighter or heavier than air in the environment.

The multilayer material can further include a remote receiver, wherein the detector is configured to deliver a signal to the remote receiver. The signal can include data associated with the identity of the at least one gas-phase chemical compound, concentration of the at least one gas-phase chemical compound, comparison of concentration of the at least one gas-phase chemical compound to baseline, or ratio of concentrations of the at least one gas-phase chemical compounds. The signal can include data associated with the identity of the reaction product, concentration of the reaction product, comparison of concentration of the reaction product to baseline, or ratio of concentrations of the reaction products. The signal can include a wireless signal. The detector can include at least one of a radio frequency identification sensor and a radio frequency identification reader. The multilayer material can include at least one of a radio frequency identification sensor and a radio frequency identification reader. The at least one signaling layer including the at least one chemical compound can include a liquid-phase chemical compound or a solid-phase chemical compound. The at least one signaling layer can include the at least one chemical compound includes the at least one gas-phase chemical compound. The at least one chemical compound can be microencapsulated in the at least one signaling layer. The at least one chemical compound can include, but is not limited to, mercaptan, carbon dioxide, 1-hexanol, sulfur hexafluoride, ethanethiol, or furaneol. The at least one chemical compound can include $^{13}CO_2$, $C^{18}O^{16}O$, $D_2O$, DHO, or other isotopically-distinctive compound. The at least one gas-phase chemical compound can be configured to be lighter or heavier than air and flow to the detector. The at least one gas-phase chemical compound can be transferred to the detector by active convection. The detector can be further configured to transmit metadata to the remote receiver. The metadata can include, but is not limited to, multilayer material identification, user identification, location of the breach in the multilayer material, detection event time, or multilayer material location. The detector can be configured to store signal data or metadata on board the detector for future readout. The detector or the remote receiver can be configured to communicate with a computing device. The computing device can be configured to activate a user interface configured to inform a wearer of the multilayer material, a co-worker, an individual, a manufacturer or a seller of the multilayer material, a supervisor, a safety official, or an insurance official.

The at least one signaling layer can include two or more chemical compounds in two or more different locations on the multilayer material, wherein the release of one or more gaseous chemical compounds derived from at least one of the two or more chemical compounds to the environment is configured to identify at least one release location on the multilayer material. The two or more different locations of the two or more chemical compounds in the at least one signaling layer can include one or more of two or more different lateral locations and two or more different layered locations on the multilayer material. In some aspects, each of the two or more different locations can have at least one distinct chemical compound. Each of the two or more different locations can have a distinct ratio of the two or more chemical compounds.

The multilayer material can include, but is not limited to, an article of clothing, a bandage, an enclosure, packaging, a surgical drape, a glove box, or a food wrapping. The at least one signaling layer can include two or more chemical compounds in a same location on the multilayer material, wherein the ratio of two or more gaseous chemical compounds derived from the two or more chemical compounds identifies the multilayer material or identifies the same location on the multilayer material.

A method for detecting a breach in a multilayer material is described herein that includes releasing at least one gas-phase chemical compound into an environment, the at least one gas-phase chemical compound produced from at least one chemical compound within at least one signaling layer of the multilayer material upon exposure of the at least one chemical compound to the environment, wherein the at least one signaling layer is enclosed within a flexible inner layer and a flexible outer layer of the multilayer material, and wherein the flexible outer layer is substantially impermeable to the environment; and detecting the at least one gas-phase chemical compound or a reaction product thereof in the environment. The method can further include communicating the detected at least one gas-phase chemical compound or the detected reaction product thereof in the environment via a signal from a detector to a remote receiver.

In some aspects, detecting the at least one gas-phase chemical compound includes detecting with at least one chemical sensor can be configured to detect the at least one chemical compound or the reaction product thereof. In some aspects, detecting the at least one gas-phase chemical compound includes detecting with at least one of a radio-frequency identification (RFID) sensor and an RFID reader. Detecting the at least one gas-phase chemical compound in the environment can indicate a breach of the multilayer material. Detecting the at least one gas-phase chemical compound in the environment can include measuring one or more absolute levels of the at least one gas-phase chemical compound or the reaction product thereof. Detecting the at least one gas-phase chemical compound in the environment can further include measuring one or more comparisons between the one or more absolute levels and one or more baseline levels of the gas-phase chemical compound. Detecting the at least one gas-phase chemical compound in the environment can further include detecting the at least one gas-phase chemical compound remotely in the environment. Detecting the at least one gas-phase chemical compound in the environment can further include measuring the rate of change of concentration of the at least one gas-phase chemical compound or the reaction product thereof. Detecting the at least one gas-phase chemical compound in the environment can further include identifying the at least one gas-phase chemical compound. Detecting the at least one gas-phase chemical compound in the environment can further include detecting a reaction product due to a reaction of the at least one gas-phase chemical compound and the environment. Detecting the at least one gas-phase chemical compound in the environment can further include detecting the gas-phase chemical compound due to a reaction of the at least one chemical compound and the environment. The method for detecting a breach in a multilayer material can further include communicating the detected at least one gas-phase chemical compound or the detected reaction product thereof in the environment via a signal from a detector to a remote receiver. The signal from the detector to the remote receiver can include a wireless signal.

In some aspects, the at least one gas-phase chemical compound can be substantially removed from the environment within a specified time. The at least one gas-phase chemical compound can be substantially removed from the environment by a chemical reaction with at least one normal component of the atmosphere. The at least one gas-phase chemical compound can be substantially removed from the environment by a chemical reaction with a chemical released or exposed subsequent to detection of the at least one gas-phase chemical compound. The at least one gas-phase chemical compound can be substantially removed from the environment by condensation. The at least one gas-phase chemical compound can be substantially removed from the environment by photodissociation. The at least one gas-phase chemical compound can be substantially removed from the environment by active convection. The active convection can be continuous or can be activated by detection of the at least one gas-phase chemical compound. The at least one gas-phase chemical compound can be substantially removed from the environment by passive convection. The at least one gas-phase chemical compound can be lighter or heavier than air in the environment.

The method for detecting a breach in a multilayer material can further include microencapsulating the at least one chemical compound in the at least one signaling layer. The method can further include transmitting metadata from the detector to the remote receiver. The method can further include storing signal data or metadata on board the detector for future readout. The metadata can include, but is not limited to, multilayer material identification, user identification, location of the breach in the multilayer material, detection event time, or multilayer material location. The method can further include communicating via the detector or the remote receiver to a computing device.

In some aspects, the at least one signaling layer can include two or more chemical compounds in a same location on the multilayer material, wherein the ratio of two or more gaseous chemical compounds derived from the two or more chemical compounds identifies the multilayer material or identifies the same location on the multilayer material. The at least one signaling layer can include two or more chemical compounds in two or more different locations on the multilayer material, wherein the release of one or more gaseous chemical compounds derived from at least one of the two or more chemical compounds to the environment is configured to identify at least one release location on the multilayer material. The two or more different locations of the two or more chemical compounds in the at least one signaling layer can include one or more of two or more different lateral locations and two or more different layered locations on the multilayer material. In some aspects, each of the two or more different locations can include at least one distinct chemical compound. In some aspects, each of the two or more different locations can include a distinct ratio of the two or more chemical compounds.

A system is described herein that includes a multilayer material including a flexible inner layer and a flexible outer layer configured to enclose at least one signaling layer including at least one chemical compound; wherein the flexible outer layer is substantially impermeable to an environment and to the at least one chemical compound in the at least one signaling layer; and wherein the at least one chemical compound within the at least one signaling layer is configured to produce at least one gas-phase chemical compound configured to be released into the environment upon exposure to the environment; and a detector configured to detect the at least one gas-phase chemical compound or a reaction product thereof in the environment.

In some aspects, the detector can be configured to form a layer of the multilayer material. The detector can be configured to operate in contact with the multilayer material. The detector is configured operate at a distance from the multilayer material. The detector can be configured to operate as one or more of a portable unit, a handheld unit, or a unit embedded into walls, furniture, or instruments. The system can further include a remote receiver, wherein the detector is configured to deliver a signal to the remote receiver. The signal can include, but is not limited to, data associated with the identity of the at least one gas-phase chemical compound, concentration of the at least one gas-phase chemical compound, comparison of concentration of the at least one gas-phase chemical compound to baseline, or ratio of concentrations of the at least one gas-phase chemical compounds. The signal can include, but is not limited to, data associated with the identity of the reaction product, concentration of the reaction product, comparison of concentration of the reaction product to baseline, or ratio of concentrations of the reaction products. The signal can include a wireless signal.

A system for use on a computer is described herein that includes a non-transient computer-readable medium including instructions for analyzing a signal to a detector indicating a breach of a multilayer material, wherein the multilayer material includes a flexible inner layer and a flexible outer layer configured to enclose at least one signaling layer including at least one chemical compound; wherein the flexible outer layer is substantially impermeable to an environment and to the at least one chemical compound in the at least one signaling layer; and wherein the at least one chemical compound within the at least one signaling layer is configured to produce at least one gas-phase chemical compound configured to be released into the environment upon exposure of the at least one chemical compound to the environment, and a non-transient computer-readable medium including instructions for analyzing metadata provided to the detector. The system can further include instructions for analyzing data from a remote receiver, wherein the remote receiver is configured to receive a second signal transmitted from the detector indicating the breach in the multilayer material. The metadata can include, but is not limited to, multilayer material identification, user identification, location of the breach in the multilayer material, detection event time, or multilayer material location. The system including the computer can be configured to inform a wearer of the material, a co-worker, a nearby individual, a manufacturer or a seller of the multilayer material, a supervisor, a safety official, or an insurance official. The detector can be configured to transmit metadata to the remote receiver. The detector can be configured to store signal data or metadata on board the detector for future readout.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
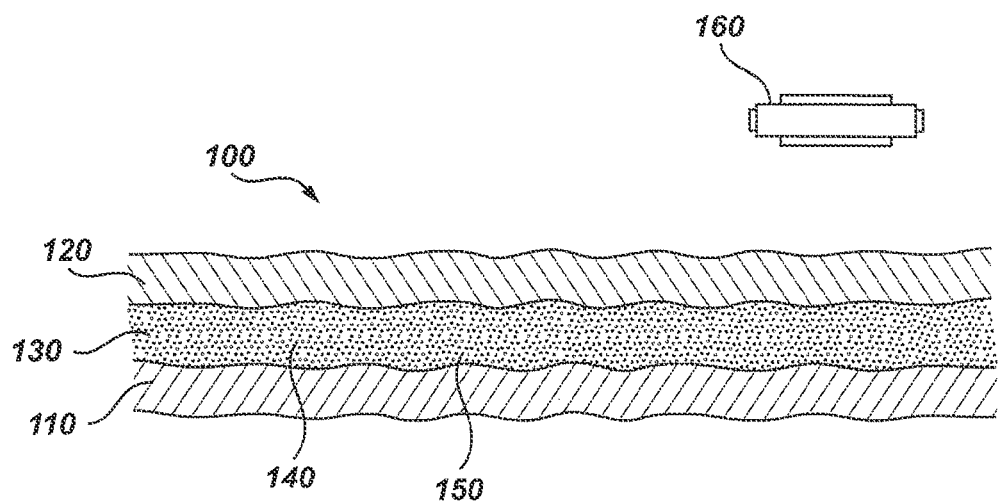
FIG. 1 depicts a diagrammatic view of one aspect of an embodiment of a material or article of clothing.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present application uses formal outline headings for clarity of presentation. However, it is to be understood that the outline headings are for presentation purposes, and that different types of subject matter may be discussed throughout the application (e.g., method(s) may be described under composition heading(s) and/or kit headings; and/or descriptions of single topics may span two or more topic headings). Hence, the use of the formal outline headings is not intended to be in any way limiting.

A flexible multilayer material incorporated in an article of clothing worn by a user or incorporated in an enclosure, for example, a bandage, packaging, a surgical drape, a glove box, or a food wrapping, is described herein that includes a protective, or impermeable or semi-permeable, barrier layer enclosing at least one signaling layer configured to signal a breach in the multilayer material. A detector is configured to detect a gas-phase chemical compound released from the at least one signaling layer following a breach of the multilayer material. The multilayer material is configured to release the gas-phase chemical compound from the at least one signaling layer to signal to the detector indicating a breach of the multilayer material. The signal from the detector is configured to notify and warn a wearer of the need to re-glove in the event that his or her multilayer material becomes torn or punctured with the result of exposing the wearer to a possibly hazardous material. The detector can be physically isolated from the signaling layer and in contact with the multilayer material, distal to the site of the breach. Alternatively, the detector can be physically isolated from, i.e., remote from, the multilayer material and physically situated away from and not in contact with the site of the breach or the multilayer material. In a clean room setting, a multilayer material can include at least one signaling layer including at least one chemical compound that can be released as a gas-phase chemical compound, wherein the gas-phase chemical compound can be detected by a detector indicating a breach of at least a portion of the multilayer material. The detector can be configured to notify or warn a clean room worker of a possible contamination of the worker or of the clean room. A multilayer material is described herein that includes a flexible inner layer and a flexible outer layer configured to enclose at least one signaling layer including at least one chemical compound; wherein the flexible outer layer is substantially impermeable to an environment and to the at least one chemical compound in the at least one signaling layer; and wherein the at least one chemical compound within the at least one signaling layer is configured to produce at least one gas-phase chemical compound configured to be released into the environment upon exposure of the at least one chemical compound to the environment. The at least one signaling layer can include a strata of layers that form the signaling layer. A system can include the multilayer material and a detector configured to detect the at least one gas-phase chemical compound indicating the breach of the multilayer material.

The detector can be configured to operate as a portable unit, a handheld unit, or a unit embedded into walls, furniture, or instruments. The at least one gas-phase chemical compound can be substantially removed from the environment within a specified time by various methods in order to lower the baseline levels of the gas-phase chemical compound for detection by the detector. The at least one gas-phase chemical compound can be substantially removed from the environment by a chemical reaction with at least one normal component of the atmosphere; by a chemical reaction with a chemical released or exposed subsequent to detection of the at least one gas-phase chemical compound; by condensation; by photodissociation; by active convection, e.g., wherein the active convection is continuous or is activated by detection of the at least one gas-phase chemical compound; or by passive convection, e.g., wherein the at least one gas-phase chemical compound is lighter or heavier than air in the environment.

Lowering the baseline levels of the gas-phase chemical compound for detection by the detector can refer to a process wherein the gas-phase chemical compound is vaporized and reacts with an element or compound in the air, e.g., oxygen or water vapor, on a suitable timescale of seconds to minutes, such that the concentration of the gas-phase chemical compound will drop quickly once the source, e.g., the breached glove, is removed. Alternatively, the gas-phase chemical compound released into the environment can be removed by convection (air exchange), especially if it is heavier or lighter than the atmosphere in the environment. The detector can be attached to the multilayer material or can be separated and remote from the multilayer material. When the gas-phase chemical compound is released from the breach site on the multilayer material, the gas-phase chemical compound will travel through the air by diffusion or convection to generate one or more signals at the detector. Hazardous material can include, but is not limited to, hazardous chemicals, contaminants, or pathogens, e.g., bacteria, virus, fungi, or prion.

In some aspects, the detector can be configured to transmit a wireless signal to a remote receiver. The detector can transmit metadata related to the identity of the damaged multilayer material, identity of the individual wearing the multilayer material, the location of the breach event in the multilayer material, and the date and the time of the breach event. This information can be communicated to the receiver or computing device and stored for future reference.

A system is described herein that includes a multilayer material including a flexible inner layer and a flexible outer layer configured to enclose at least one signaling layer including at least one chemical compound; wherein the flexible outer layer is substantially impermeable to an environment and to the at least one chemical compound in the at least one signaling layer; and wherein the at least one chemical compound within the at least one signaling layer is configured to produce at least one gas-phase chemical compound configured to be released into the environment upon exposure to the environment; and a detector configured to detect the at least one gas-phase chemical compound or a reaction product thereof in the environment. The system including the multilayer material and the detector can be configured to detect the at least one gas-phase chemical compound or a reaction product thereof in the environment indicating a breach of the multilayer material. The reaction product of the at least one gas-phase chemical compound can be produced by reaction with environmental components including, but not limited to, reactive oxidation in the atmosphere with the gas-phase chemical compound; photoreaction with the gas-phase chemical compound; or reaction of the gas-phase chemical compound with one or more bodily fluids.

One or more chemical compounds that are configured to form a gas-phase chemical compound from a solid-phase, liquid-phase, gas-phase, or liquid-gas transition chemical compound can be incorporated within at least one signaling layer of the multilayer material configured to be released from the at least one signaling layer as one or more gas-phase chemical compounds to signal breach of the multilayer material. The one or more chemical compounds can have a high vapor pressure to be volatile but not corrosive or dangerous to the user. The gas-phase chemical compound can be configured to be easily detected at low concentrations, and to be promptly removed from the environment by chemical or physical processes such that successive releases can be detected. In particular, the one or more compounds may be substantially denser or less dense than air, causing them to flow preferentially down or up, or may be substantially the same density as air. The one or more chemical compounds include, but are not limited to, volatile compounds that are not corrosive or dangerous to a user, such as mercaptan, carbon dioxide, 1-hexanol, sulfur hexafluoride, ethanethiol, furaneol, or an isotopically-labeled compound. The one or more chemical compounds can include compounds similar to those normally present in the environment, but having some detectable distinguishing characteristic. Distinguishing characteristics may include chemical substitutions or isotopic substitutions, e.g., substitution of deuterium for hydrogen, substitution of isotope $^{18}O$ for isotope $^{16}O$, or substitution of isotope $^{13}C$ for isotope $^{12}C$, wherein the at least one chemical compound includes $^{13}CO_2$, $C^{18}O^{16}O$, $D_2O$, DHO, or other isotopically-distinctive compound.

A flexible multilayer material can be incorporated in an article of clothing worn by a user, or in a bandage, an enclosure, packaging, a surgical drape, a glove box, or a food wrapping. The flexible multilayer material can be incorporated into an article of clothing or into various forms of packaging to maintain sterility of an enclosed item. The flexible multilayer material can be incorporated into packaging to contain a chemical or biohazardous material and to maintain/monitor containment of the material.

With reference to the figures, and with reference now to FIGS. 1, 2, 3, and 4 depicted is one aspect of a material, an article of clothing, or a system that may serve as an illustrative environment of and/or for subject matter technologies, for example, a multilayer material including a flexible inner layer and a flexible outer layer configured to enclose at least one signaling layer including at least one chemical compound; wherein the flexible outer layer is substantially impermeable to an environment and to the at least one chemical compound in the at least one signaling layer; and wherein the at least one chemical compound within the at least one signaling layer is configured to produce at least one gas-phase chemical compound configured to be released into the environment upon exposure of the at least one chemical compound to the environment, or, for example, a system comprising a multilayer material including a flexible inner layer and a flexible outer layer configured to enclose at least one signaling layer including at least one chemical compound; wherein the flexible outer layer is substantially impermeable to an environment and to the at least one chemical compound in the at least one signaling layer; and wherein the at least one chemical compound within the at least one signaling layer is configured to produce at least one gas-phase chemical compound configured to be released into the environment upon exposure of the at least one chemical compound to the environment, and a detector configured to detect the at least one gas-phase chemical compound or a reaction product thereof in the environment. Accordingly, the present disclosure describes certain specific materials, articles of clothing, systems, or methods of FIGS. 1, 2, 3, and 4; and describes embodiments including certain specific materials, articles of clothing and systems. Those having skill in the art will appreciate that the specific materials, articles of clothing, systems, or methods described herein are intended as merely illustrative of their more general counterparts.

Referring to FIG. 1, depicted is a partial diagrammatic view of one aspect of an embodiment of a system including a multilayer material 100 including a flexible inner layer 110 and a flexible outer layer 120 configured to enclose a signaling layer 130 including at least one chemical compound (solid, liquid, gas or liquid-gas transition) 140 within the signaling layer 130; wherein the flexible outer layer 120 is substantially impermeable to an environment and to the at least one chemical compound 140 in the signaling layer 130; and wherein the at least one chemical compound 140 within the signaling layer 130 is configured to produce at least one gas-phase chemical compound 150 configured to be released into the environment upon exposure of the at least one chemical compound 140 to the environment. The signaling layer 130 includes the chemical compound 140 under pressure in a gas phase, gas-liquid phase, liquid phase, or solid phase and configured to be released as the gas-phase chemical compound 150. A detector 160 is configured to detect the gas-phase chemical compound 150 indicating the breach of the multilayer material 100.

Figure 2:
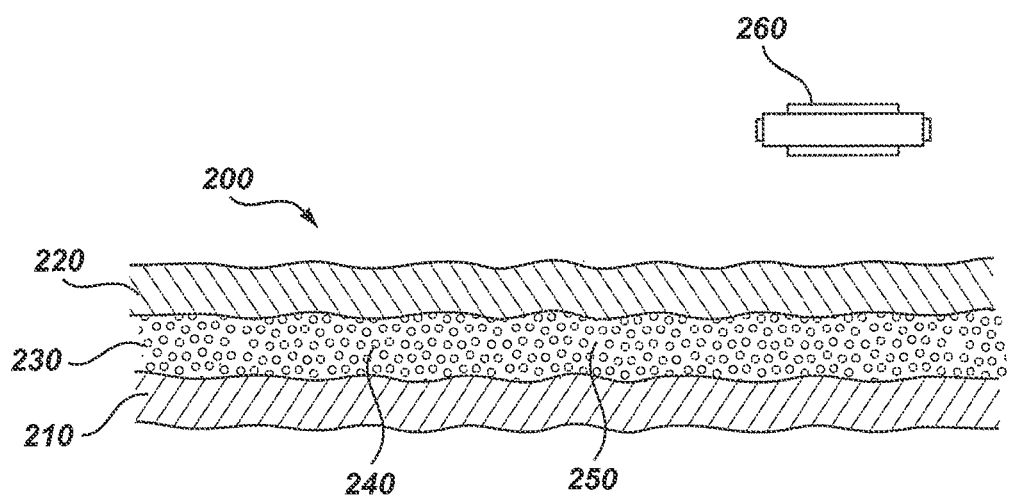
FIG. 2 depicts a diagrammatic view of one aspect of an embodiment of a material or article of clothing.

Referring to FIG. 2, depicted is a partial diagrammatic view of one aspect of an embodiment of a system including a multilayer material 200 including a flexible inner layer 210 and a flexible outer layer 220 configured to enclose a signaling layer 230 including at least one chemical compound (solid, liquid, gas or liquid-gas transition) 240 within the signaling layer 230; wherein the flexible outer layer 220 is substantially impermeable to an environment and to the at least one chemical compound 240 in the signaling layer 230; and wherein the at least one chemical compound 240 within the signaling layer 230 is configured to produce at least one gas-phase chemical compound 250 configured to be released into the environment upon exposure of the at least one chemical compound 240 to the environment. The signaling layer 230 includes the chemical compound 240 embedded within a solid or semi-solid signaling layer 230. The gas-phase chemical compound 250 is under pressure in a gas phase, gas-liquid phase, liquid phase, or solid phase, within the solid or semi-solid signaling layer 230. The signaling layer 230 includes the chemical compound 240 under pressure in a gas phase, gas-liquid phase, liquid phase, or solid phase. A detector 260 is configured to detect the gas-phase chemical compound 250 indicating the breach of the multilayer material 200.

Figure 3:
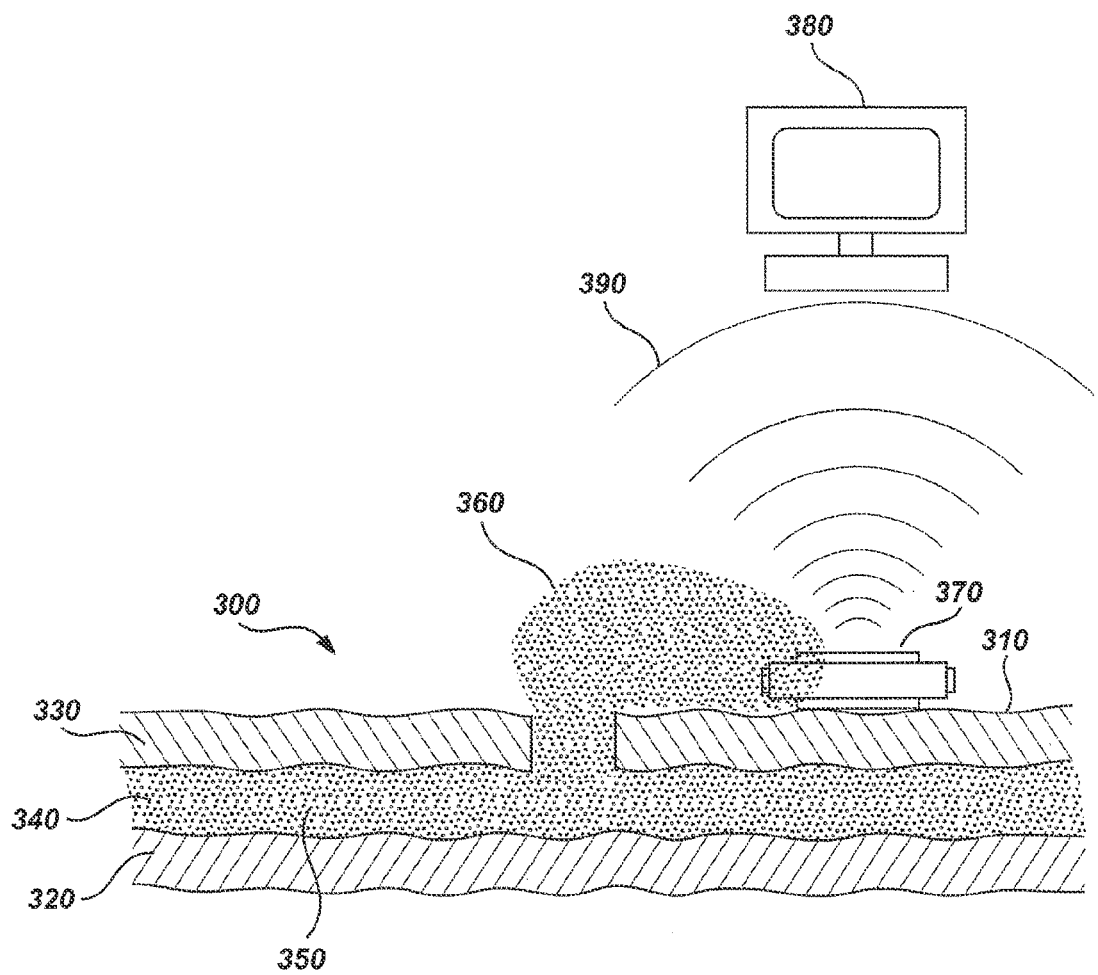
FIG. 3 depicts a diagrammatic view of one aspect of an embodiment of a system including a material and a detector to remotely indicate a breach in the material.

Referring to FIG. 3, depicted is a partial diagrammatic view of one aspect of an embodiment of a system 300 comprising a multilayer material 310 including a flexible inner layer 320 and a flexible outer layer 330 configured to enclose a signaling layer 340 including at least one chemical compound (solid, liquid, gas or liquid-gas transition) 350 within the signaling layer 340; wherein the flexible outer layer 330 is substantially impermeable to an environment and to the at least one chemical compound 350 in the signaling layer 340; and wherein the at least one chemical compound 350 within the signaling layer 340 is configured to produce at least one gas-phase chemical compound 360 configured to be released into the environment upon exposure of the at least one chemical compound 350 to the environment. A detector 370 is attached to the multilayer material 310 and is configured to remotely detect the signal; and a remote receiver 380 is configured to receive a second signal 390 transmitted from the detector 370 indicating the breach in the multilayer material 310.

Figure 4:
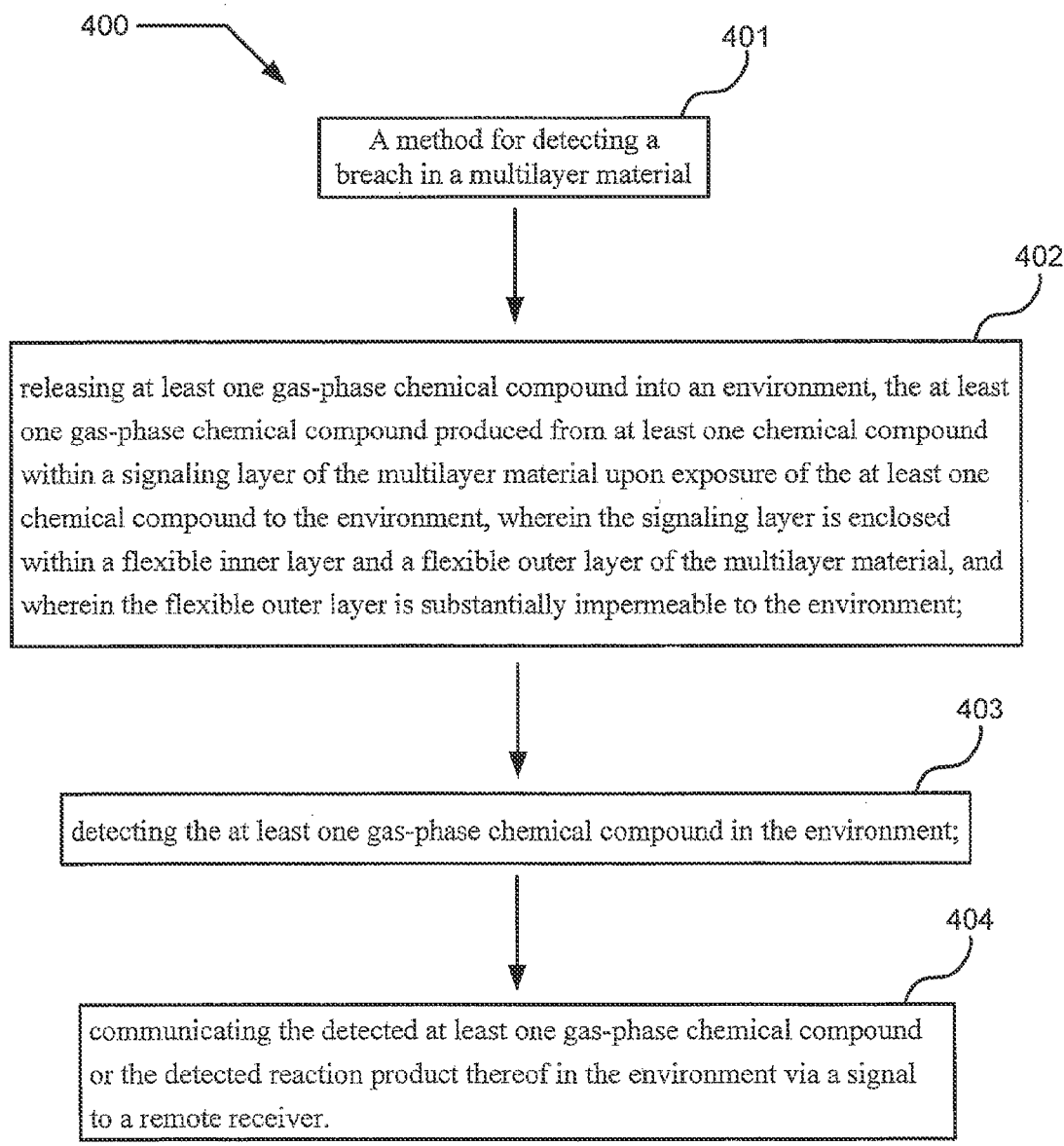
FIG. 4 depicts a diagrammatic view of one aspect of an embodiment of a method for remotely indicating a breach in the material.

FIG. 4 illustrates a method for detecting a breach in a multilayer material 401 comprising releasing 402 at least one gas-phase chemical compound into an environment, the at least one gas-phase chemical compound produced from at least one chemical compound within a signaling layer of the multilayer material upon exposure of the at least one chemical compound to the environment, wherein the signaling layer is enclosed within a flexible inner layer and a flexible outer layer of the multilayer material, and wherein the flexible outer layer is substantially impermeable to the environment; detecting 403 the at least one gas-phase chemical compound in the environment; communicating 404 the detected at least one gas-phase chemical compound in the environment via a wireless signal to a remote receiver.

Multilayer Material Including a Flexible Inner Layer and a Flexible Outer Layer Configured to Enclose at Least One Signaling Layer Including at Least One Chemical Compound Multilayer materials for gloves or clothing including a protective barrier, e.g., impermeable or semi-permeable multilayer material, can include a flexible inner layer and a flexible outer layer configured to enclose at least one signaling layer including at least one chemical compound; wherein the flexible outer layer is substantially impermeable to an environment and to the at least one chemical compound in the at least one signaling layer; and wherein the at least one chemical compound within the at least one signaling layer is configured to produce at least one gas-phase chemical compound configured to be released into the environment upon exposure of the at least one chemical compound to the environment. The multilayer material can be constructed and reinforced by one or more processes including, but not limited to, dip forming or spraying onto a glove mold. Multilayer material for examination gloves used in industrial laboratories, bioprocessing plants, research laboratories, hospitals, and clinics can be constructed from nitrile by dipping glove forms. Multiple layers of nitrile can be added in a multi-dipping manufacturing process described in U.S. Pat. No. 6,347,408 entitled "Powder-free Gloves Having a Coating Containing Cross-linked Polyurethane and Silicone and Method of Making the Same" issued to Yeh et al. on Feb. 19, 2002, which is incorporated herein by reference.

Multilayer material for protective gloves or suits, e.g., impermeable or semi-permeable multilayer material, can be produced from a variety of materials including, but not limited to, latex, polymers, elastomers, rubber, or plastic. The medical glove can include a multilayer material comprised of latex or a synthetic polymer, for example, poly(trans-2-chloro-1,3-butadiene), commonly known as poly(chloroprene) (available from DuPont Performance Elastomers L.L.C., Wilmington, Del. 19809).

One or more chemical compounds that are configured to form a gas-phase chemical compound from a solid-phase, liquid-phase, gas-phase, or liquid-gas transition chemical compound can be incorporated within at least one signaling layer of the multilayer material, such as protective material for a protective suit or gloves, e.g., impermeable or semi-permeable multilayer material, configured to be released from the at least one signaling layer as one or more gas-phase chemical compounds to signal breach of the multilayer material. The one or more chemical compounds have a high vapor pressure to be volatile but not corrosive or dangerous to the user. The one or more chemical compounds including, but are not limited to, mercaptan, carbon dioxide, 1-hexanol, sulfur hexafluoride, ethanethiol, furaneol, or an isotopically-labeled compound, can be incorporated within at least one signaling layer of the multilayer material to signal breach of the multilayer material incorporated into a protective suit or protective gloves. Chemical compounds can be incorporated in the at least one signaling layer within and between the flexible inner layer and the flexible outer layer of multilayer material by mixing the signal chemicals with latex or polymer liquids prior to forming (i.e., polymerizing or vulcanizing) a layer of the fabric. For example, methods and compositions for making a multilayer fabric from a layer of polypropylene that is laminated with a polyethylene film is described in U.S. Pat. No. 7,225,476 entitled "Protective Clothing Against Biological Agents" issued to Cerbini and Lo loco on Jun. 5, 2007, which is incorporated herein by reference.

Multi-dipping manufacturing processes include a membrane of multi-layer construction includes one or more flexible inner layers, one or more flexible outer layers, and one or more signaling layers which can serve as a reservoir for one or more chemical compounds including, but not limited to, a gas-phase chemical compound, a liquid-phase chemical compound, or a solid-phase chemical compound, wherein the one or more chemical compounds can pass through one or more permeable or semi-permeable signaling layers to make the one or more gas-phase chemical compounds available on the outside of the membrane released into the environment in the event of a breach of the multilayer material. Substantially impermeable or semipermeable outer layers can transmit the one or more gas-phase chemical compounds upon rupture or piercing of the flexible outer layer and completely contain the substances at all other times. See, e.g., U.S. Pat. No. 5,549,924 entitled "Method of Forming A Membrane, Especially A Latex or Polymer Membrane, Including A Deactivating Barrier and Indicating Layer" issued to Shlenker et al. on Aug. 27, 1996, which is incorporated herein by reference.

In an embodiment, gloves constructed of a multilayer material including a flexible inner layer and a flexible outer layer configured to enclose at least one signaling layer including at least one chemical compound can provide a flexible protective, e.g., impermeable or semi-permeable, medical glove. The flexible protective, e.g., impermeable or semi-permeable, medical glove can have a thin glove wall comprising at least a flexible outer layer of a first material having a thickness of between about 1 mil (1 mil=one-thousandth of an inch) to about 40 mils and at least a flexible inner layer of a second material having a thickness of between about 0.3 mils to about 30 mils wherein the first material and the second material form at least the walls of at least one signaling layer storing a gas-phase chemical compound, a liquid-phase chemical compound, or a solid-phase chemical compound. The at least one signaling layer storing the gas-phase chemical compound, liquid-phase chemical compound, or solid-phase chemical compound can have a thickness ranging between about 10 mils to about 100 mils, but in some areas of the glove, particularly while the glove is being worn, the at least one signaling layer can become temporarily compressed to less than 1 mil in thickness. Alternatively, or at the same time, the at least one signaling layer in some areas of the glove can be expanded by design or while the glove is being worn can become temporarily expanded to a thickness exceeding 500 mils. At the end of the glove where the hands would be first inserted, the at least one signaling layer can be open or can be closed. Alternatively, the glove can be reversibly opened or closed using for example a zip-lock or other sealing seam between the glove layers at the opening of the compartment, to allow the individual that wears the glove to increase or reduce the amount of gas-phase chemical compound, liquid-phase chemical compound, or solid-phase chemical compound in the at least one signaling layer of the glove. The at least one signaling layer can be closed while the glove is in use. The glove can be as flexible as a conventional medical glove, to permit the gloved hand to easily and adequately perform delicate, dexterous, and complex hand work including, for example, the hand work of a surgeon, a medical doctor, a dentist, a laboratory worker, a health care worker, a law enforcement worker, a hospital worker and like workers. The glove wall can be constructed from almost any material or combination of materials provided that at least the surface of the inner glove layer and at least the surface of the outer glove layer are liquid-impermeable. The glove wall layers can be made using thin flexible layers of rubber and/or plastic materials. See, e.g., U.S. Pat. No. 5,335,373 entitled "Protective Medical Gloves and Methods for Their Use" issued to Dangman et al. on Aug. 9, 1994.

The multilayer material for medical gloves or clean room gloves, as disclosed herein, can be constructed from latex, polyurethane, polyethylene, rubber and other elastomers and polymers by using molds or by dipping or spraying hand forms. For example, multiple layers of latex can be added in a multi-dipping manufacturing process. A membrane formed from liquid latex, solvent cast membranes, liquid polymers, or elastomers can be formed by dip forming, the use of fluidized beds, or spraying the liquid material onto a former. After deposit of one or more flexible inner layers, one or more signaling layers can be deposited. Thereafter, one or more flexible outer layers can be formed and the membrane can be cured or set according to conventional techniques.

Suitable polymers for use in producing membranes for a multilayer material include prepolymers, i.e., low molecular weight polymers and polymer precursors, prepolymers and polymer precursors dissolved in solvents, liquid monomers, and liquid monomers dissolved in solvents. Specific examples include low molecular weight polymers such as silicone rubber (polydimethyl siloxane: $HO-(Si-(CH_3)_2-O-)_n-H$) with n from 2 to 200; polymer precursors such as low molecular weigh diol, e.g., $HO-((CH_2)_4-O)_{18}-H$ and low molecular weight diisocyanate, e.g., $OCN-C_6H_6-CH_2-C_6H_6-NCO$ which when mixed and polymerized form polyurethane. Solvents for low molecular weight polymers include, but are not limited to, xylene and n-hexane. Suitable solvents for polymer precursors include, but are not limited to, dimethyl formamide and dimethyl sulfoxide. Liquid monomers include, but are not limited to, alpha-alkyl cyanoacrylate, where the alkyl group can be -methyl, -ethyl, -propyl. Solvents for liquid monomers include, but are not limited to, dimethyl formamide. Prepolymer, polymer, and polymer precursors include, but are not limited to, mixtures of one or more prepolymers, polymers, or polymer precursors. See, e.g., U.S. Pat. No. 5,549,924 entitled "Method of Forming A Membrane, Especially A Latex or Polymer Membrane, Including A Deactivating Barrier and Indicating Layer" issued to Shlenker et al. on Aug. 27, 1996 which is incorporated herein by reference.

Multilayer gloves or multilayer clothing using multilayer membranes include, but are not limited to, a structural material including latex rubber, cis-1,4-polyisoprene, cis-polybutadiene, neoprene rubber, nitrile rubber, silicone rubber, cellulose acetate plastic, vinyl plastic, polyethylene plastic, polypropylene plastic, polyvinyl chloride plastic, polyvinyl acetate plastic, polystyrene plastic, polymethyl methyl-acrylate plastic, polyacrylonitrile plastic, vinyllite plastic, saran plastic, polytetrafluoroethylene plastic, polytrifluorochloroethylene plastic, polycaprolactam plastic, polyester plastic, urea formaldehyde plastic, polyurethane plastic, isotactic polypropylene plastic, nylon plastic, rayon plastic, polyamide plastic, phenolic plastic, silicone plastic, silk fiber, cotton fiber, cellulose fiber, wool fiber, animal skin, animal intestinal tissue, animal connective tissue, metallic fiber, mineral fiber and mixtures thereof. See, e.g., U.S. Pat. No. 5,335,373, which is incorporated herein by reference.

Chemical compounds or gas-phase chemical compounds, e.g., mercaptan, carbon dioxide, 1-hexanol, sulfur hexafluoride, ethanethiol, furaneol, or an isotopically-labeled compound, can be incorporated within a flexible inner layer of the medical glove to be released as a gas-phase chemical compound to signal when the glove has been breached. Chemical compounds can be incorporated into the at least one signaling layer within and between the flexible inner layer and the flexible outer layer of multilayer material gloves by mixing the chemicals with latex or polymer liquids prior to dipping the glove formers and adding the next layer. For example, methods for making multilayer membranes incorporating one or more signaling layers or congealing substances are provided. Conventional dipping, spraying or other sheet forming techniques can be used to create an initial flexible inner layer containing an elastomer material such as latex, solvent cast membranes, liquid polymers or polymer films. A second layer can be created by coating or dipping (with or without a coagulant) latex, liquid polymers, solvent cast membranes or liquid films containing an indicator chemical such as a volatile chemical, aroma, gas, liquid, dye, crystal, or colored agent. Using conventional methods (e.g., dipping, spraying, molding) one or more additional membrane layers can be added to contain the indicator chemical. Methods of forming the one or more flexible inner layer and one or more flexible outer layers of multilayer membranes can include, but is not limited to: dip coating, spray coating, fluidized bed deposition, vapor deposition, electrical discharge deposition, vacuum deposition, centrifugal coating and extrusion. Gas-phase chemical compounds, e.g., sulfur hexafluoride, can be infused (bubbled) into the latex or polymer liquid prior to dipping a glove former into the liquid. One or more additional layers of latex or polymer can be applied to prevent diffusion of the sulfur hexafluoride gas present in the latex or polymer layer. See, e.g., U.S. Pat. No. 5,549,924, entitled "Method of Forming A Membrane, Especially A Latex or Polymer Membrane, Including A Deactivating Barrier and Indicating Layer" issued to Shlenker et al. on Aug. 27, 1996, which is incorporated herein by reference.

Multilayer material for protective, e.g., impermeable or semi-permeable, gloves or clothing for medical or clean room applications can be used in industrial laboratories, bioprocessing plants, research laboratories, hospitals, and clinics. The gloves or clothing are constructed from nitrile, neoprene, or natural rubber by dipping glove forms. Multiple layers of nitrile, neoprene, or natural rubber are added in a multi-dipping manufacturing process described in U.S. Pat. No. 6,347,408 entitled "Powder-free Gloves Having a Coating Containing Cross-linked Polyurethane and Silicone and Method of Making the Same" issued to Yeh et al. on Feb. 19, 2002, which is incorporated herein by reference. A glove former is dipped in a coagulant dispersion comprised of calcium nitrate, calcium carbonate powders, wetting agents and water (or alcohol for alcohol based coagulant dispersion). The coagulant layer deposited on the glove former is allowed to dry. The glove former with the dried coagulant layer is then dipped into compounded nitrile latex maintained at about 68° F. to about 86° F. The glove former with a first nitrile layer is leached with water for 3 to 10 minutes at 78-110° F. and then dried. The dipping process is repeated to add additional layers of nitrile.

The multilayer material for protective, e.g., impermeable or semi-permeable, gloves or clothing constructed of nitrile, neoprene, or natural rubber can have a thickness of at least about 0.003 inches. The thickness of the multilayer material can range between about 0.004 inches and about 0.010 inches, or the-glove thickness can range between about 0.005 and about 0.008 inches.

The multilayer material constructed of nitrile, neoprene, or natural rubber can exhibit a tensile strength of greater than about 1300 psi, or greater than about 2000 psi, or greater than about 2600 psi. The stress at 500% of the multilayer material can be less than about 3000 psi, less than about 2000 psi or less than about 1000 psi. The multilayer material have an elongation to break greater than about 200%, greater than about 400% or greater than about 500%.

The multilayer material constructed of nitrile, neoprene, or natural rubber can exhibit a dry kinetic coefficient of friction (COF) of less than about 0.5 for the donning (coated) inner surface and greater than about 0.5 for the gripping (uncoated) outer surface. The dry kinetic COF can be less than about 0.4 for the donning surface and greater than about 0.6 for the gripping surface, or the dry kinetic COF can be less than about 0.3 for the donning surface and greater than about 0.7 for the gripping surface.

Natural rubber material coated on their interior with a polyurethane coating can exhibit a tensile strength of greater than about 2000 psi, greater than about 3000 psi, or greater than about 4000 psi. The stress at 500% of the polyurethane coated natural rubber material can be less than about 2000 psi, less than about 1000 psi, or less than about 800 psi. The polyurethane coated natural rubber material can have an elongation to break greater than about 200%, greater than about 500%, or greater than about 800%.

The dry kinetic COF of the polyurethane coated natural rubber multilayer material can be less than about 0.5 for the donning surface and greater than about 0.5 for the gripping surface. The dry kinetic COF can be less than about 0.4 for the donning surface and greater than about 0.6 for the gripping surface, or the dry kinetic COF can be less than about 0.3 for the donning surface and greater than about 0.7 for the gripping surface.

Nitrile rubber multilayer material coated on their interior with the polyurethane coating of the invention can exhibit a tensile strength of greater than about 2000 psi, greater than about 2500 psi, or greater than about 3000 psi. The stress at 500% of the polyurethane coated nitrile multilayer material as disclosed herein can be less than about 3000 psi, less than about 2000 psi, or less than about 1000 psi. The polyurethane coated nitrile multilayer material can have an elongation to break greater than about 200%, greater than about 400%, or greater than about 500%.

The dry kinetic COF of the polyurethane coated nitrile rubber multilayer material can be less than about 0.5 for the donning surface and greater than about 0.4 for the gripping surface. Preferably, the dry kinetic COF can be less than about 0.4 for the donning surface and greater than about 0.6 for the gripping surface, or the dry kinetic COF can be less than about 0.3 for the donning surface and greater than about 0.7 for the gripping surface.

Neoprene rubber multilayer material coated on their interior with the polyurethane coating of the invention can exhibit a tensile strength of greater than about 2000 psi, greater than about 2400 psi, or greater than about 2600 psi. The stress at 500% of the polyurethane coated neoprene gloves can be less than about 2000 psi, less than about 1000 psi, or less than about 800 psi. The polyurethane coated neoprene gloves can have an elongation to break greater than about 200%, greater than about 500%, or greater than about 800%.

The dry kinetic COF of the polyurethane coated neoprene rubber multilayer material can be less than about 0.5 for the donning surface and greater than about 0.5 for the gripping surface. The dry kinetic COF can be less than about 0.4 for the donning surface and greater than about 0.6 for the gripping surface, or the dry kinetic COF can be less than about 0.3 for the donning surface and greater than about 0.7 for the gripping surface. See, e.g., U.S. Pat. No. 6,347,408 entitled "Powder-free Gloves Having a Coating Containing Cross-linked Polyurethane and Silicone and Method of Making the Same" issued to Yeh et al. on Feb. 19, 2002, which is incorporated herein by reference.

A single hand-shaped ceramic mandrel can be used to manufacture a multilayer latex material for surgical glove or clothing including a flexible inner layer and a flexible outer layer configured to enclose at least one signaling layer including at least one chemical compound that is configured to release a gas-phase chemical compound from the signal layer to be released into the environment upon exposure of the at least one chemical compound to the environment. A detector can be configured to detect the gas-phase chemical compound in the environment indicating a breach of the multilayer material to warn a health care worker of the need to re-glove in the event that his glove becomes torn or punctured with the result of exposing the health care worker to a hazardous substance, e.g., a possibly contagious or life-threatening pathogen, or a biological or chemical agent. To form the multilayer material, a single layer glove can be formed by first cleaning the mandrel in a wash tank filled with water and detergent. The mandrel can be then moved, as one of a plurality of identical mandrels being carried from station to station by means of a conveyer belt, to a rinse tank where the detergent from the wash tank can be removed. After the mandrel is dried in warm air, it can be dipped in a first coagulant tank containing water and equal amounts of calcium nitrate and calcium carbonate. From the first coagulant tank, the mandrel can be dried in warm air so as to leave the mandrel covered with a powdery mold release agent by which to facilitate the removal of the double layer glove. The mandrel can then be dipped in a first latex filled tank to cover the mold release agent with a first layer of latex. The mandrel can be dried and heated to vulcanize the latex and thereby form a single layer latex glove.

The mandrel around which the multilayer latex material for the glove can now dipped in a second coagulant tank containing water and about three times more calcium carbonate, by weight, than calcium nitrate. The dip of the mandrel into the second coagulant tank can be relatively shallow compared with the dip into the first coagulant tank so that a region around the cuff of the latex glove will not be covered with mold release agent. The mandrel can be dried in warm air to leave a more effective mold release agent covering the multilayer latex material of the glove, except for the cuff area thereof. The mandrel can then be dipped in a second latex filled tank so that the first glove, including the cuff area, is now covered with latex. After being dried and heated to vulcanize the second layer of latex, first and second layers of the latex gloves can be combined to form at least one signaling layer, one over the other, which are separated by the mold release agent. Inasmuch as the cuff area of the first (i.e., inner) latex glove is not covered with a mold release agent, a latex-to-latex bond can be established between the cuff areas of the first and second latex gloves in order to hermetically seal the gloves together and form the at least one signaling layer between the inner flexible layer and the outer flexible layer of the multilayer material for the latex glove. Accordingly, an integral multilayer surgical glove can be formed over the mandrel with the mold release agent preventing the flexible inner layer and the flexible outer layer from sticking together while, at the same time, establishing a channel around the finger area of the composite glove through which air will flow, after the channel is first evacuated, in the event that the flexible outer layer of the latex glove is punctured or torn. A supply of high pressure air can be directed from a series of nozzles that are spaced around the cuff area of the multilayer material glove. Blasts of air from the nozzles simultaneously inflate and blow the now completed multilayer material glove off the mandrel into a bin. See, e.g., U.S. Pat. No. 5,911,848 entitled "Method for Making A Puncture Evident Double Layer Surgical Glove" issued to Haber et al. on Jun. 15, 1999 which is incorporated herein by reference.

One or more chemical compounds or gas-phase chemical compounds include volatile compounds that are not corrosive or dangerous to a user, e.g., mercaptan, carbon dioxide, 1-hexanol, sulfur hexafluoride, ethanethiol, furaneol, or an isotopically-labeled compound, can be added to the at least one signaling layer between the flexible inner layer and the flexible outer layer of the multilayer material glove by inflating the space between the flexible inner layer and the flexible outer layer with the gas at low pressure. After infusion of the one or more chemical compounds the gas inlet on the glove is sealed. Methods to construct gloves with a sealable gas inlet are described in U.S. Pat. No. 5,911,848 entitled "Method for Making A Puncture Evident Double Layer Surgical Glove" issued to Haber et al. on Jun. 15, 1999; Multilayer gloves with a sealed reservoir between two layers are described in U.S. Pat. No. 5,549,924 entitled "Method of Forming A Membrane, Especially A Latex or Polymer Membrane, Including A Deactivating Barrier and Indicating Layer" issued to Shlenker et al. on Aug. 27, 1996 each of which are incorporated herein by reference.

Alternatively, one or more chemical compounds, e.g., mercaptan, carbon dioxide, 1-hexanol, sulfur hexafluoride, ethanethiol, furaneol, or an isotopically-labeled compound, can be infused (bubbled) into the polymer liquid of the at least one signaling layer prior to dipping a glove former into the liquid. One or more additional signaling layers and flexible outer layers of polymer liquid are applied to prevent diffusion of the chemical compound, e.g., gas-phase chemical compound, present in the multilayer material of polymer layer.

Release of a Gas-phase Chemical Compound to a Detector Indicating a Breach of a Flexible Outer Layer in a Multilayer Material Carbon dioxide. To produce gas-phase chemical compound, carbon dioxide ($CO_2$), the at least one signaling layer can contain aqueous 0.8 moles/liter (M) sodium bicarbonate ($NaHCO_3$). An adjacent signaling layer external to the sodium bicarbonate-containing signaling layer can contain aqueous 0.26 M citric acid ($C_6H_8O_7$). Breaching the glove can occur by puncturing the flexible outer layer and the multiple signaling layers which results in a mixing reaction of sodium bicarbonate and citric acid to form gas-phase carbon dioxide ($CO_2$). The chemical reaction is:

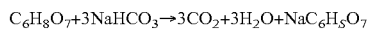

$$C_6H_8O_7 + 3NaHCO_3 \rightarrow 3CO_2 + 3H_2O + NaC_6H_5O_7$$

Isotopically-identifiable carbon dioxide can be produced by using reactants containing high percentages of $^{13}C$, $^{18}O$, or both.

1-hexanol. Gas-phase chemical compound, 1-hexanol, can be emitted from solutions of chemical compound, 1-hexanol in water, at a concentration of less than or equal to 0.01% (volume/volume). Breaching the multilayer material can occur by puncturing the flexible outer layer and the at least one signaling layer resulting in release of gas-phase 1-hexanol into the environment which can be detected in the adjoining air by open-air ionization mass spectrometry. See Buhr et al., *International Journal of Mass Spectrometry*, 221, 1-7, 2002, which is incorporated herein by reference.

Sulfur Hexafluoride.

Gas-phase chemical compound, sulfur hexafluoride, can be added to at least one signaling layer between a flexible inner layer and a flexible outer layer of the multilayer glove by inflating the space of the at least one signaling layer between the flexible inner layer and the flexible outer layer with sulfur hexafluoride gas at low pressure. Breaching the glove can occur by puncturing the flexible outer layer and the at least one signaling layer resulting in release of sulfur hexafluoride gas into the environment which can be detected in the adjoining air by open-air ionization mass spectrometry. Sulfur hexafluoride gas is available from Concorde Specialty Gases, Inc., Eatontown, N.J. 07724.

Ethanethiol and Furaneol.

Gas-phase chemical compound, ethanethiol, optionally in combination with furaneol, can be incorporated within one or more signaling layers between the flexible inner layer and the flexible outer layer of the multilayer material medical glove. Release of ethanethiol, optionally in combination with furaneol, from the at least one signaling layer can signal breach of the glove when released from a puncture or tear in the outer flexible layer of the multilayer material of the glove and detected by mass spectrometry or radio-frequency identification (RFID) detector. Ethanethiol and furaneol are available from Sigma-Aldrich, St. Louis, Mo. Signal chemicals can be incorporated within the at least one signaling layers and between the layers of multilayer gloves by mixing the chemicals with polymer liquids prior to dipping the glove formers and adding the next layer. See, e.g., U.S. Pat. No. 5,549,924 entitled "Method of Forming a Membrane, Especially a Latex or Polymer Membrane, Including a Deactivating Barrier and Indicating Layer" issued to Shlenker et al. on Aug. 27, 1996, which is incorporated herein by reference. One or more additional layers of polyurethane polymer can be applied as flexible inner layers and flexible outer layers to enclose and contain the chemical compounds.

A solution of 18 moles/liter (M) ethanethiol can be diluted ten-fold into a liquid polymer (e.g., polypropylene) and incorporated into one or more signaling layers of the multilayer material. Alternatively, a solution of 1.8 M ethanethiol can be injected into a multilayer material including at least one signaling layer including a void space between the layers. See, e.g., U.S. Pat. No. 5,549,924 entitled "Method of Forming A Membrane, Especially A Latex or Polymer Membrane, Including A Deactivating Barrier and Indicating Layer," which is incorporated herein by reference.

Detectors for One or More Chemical Compounds Released into the Environment

Detectors can use any detection technology capable of detecting specific gas-phase chemical compounds including, but not limited to, sensors based on electrochemical processes, calorimetric (heat of reaction) sensors, colorimetric (chemical reaction-caused color change) sensors, absorption or emission spectroscopic sensors including DIAL (differential infrared absorption of lasers) and FTIR (Fourier-transform infrared) spectroscopy, mass spectroscopy, and biological detectors. Detectors can be sensitive to absolute concentration, relative concentration, concentration relative to a threshold, or rate of change of concentration of one or more gas phase compounds. In some aspects, detectors including, but not limited to, mass spectrometers and infrared spectrometers, can distinguish chemicals having the same chemical composition but different isotopic composition.

In some aspects, detectors attached to individual items of clothing or worn by individual users can be compact and require little or no electric power. Such micro-detectors have been developed using a wide variety of detector technologies, typically on silicon or flexible plastic substrates.

Micro-detectors for one or more gas-phase chemicals may be integrated with passive or active radio frequency identification (RFID) tags, including RFID sensors and RFID readers. A detector can include, in part, one or more RFID tags configured as an RFID sensor to detect the one or more gas-phase chemical compounds released into the environment. The RFID circuitry may provide power to the micro-detector, either from a battery or from received RF power. The RFID circuitry may be configured to transmit information from the micro-detector to an RFID reader, including status information and information on current or past detection of one or more chemicals. In some cases, the RFID circuitry may itself act as a detector, for example by changing one or more resonant frequencies in response to the presence or concentration of a gas-phase chemical. For example, a passive RFID tag with a nominal frequency of 13.56 MHz (available from Texas Instruments, Digi-key Corp., or TagSys Co.) can be coated with a polymer sensing film and positioned in a low-volume analyte flow cell as part of the detector. A copolymer of tetrafluoroethylene and sulfonyl fluoride vinyl ether (sold as Nafion®, Sigma-Aldrich Chem. Co., St. Louis, Mo.) can be used to coat the antenna of an RFID tag. The response selectivity of Nafion® copolymer (tetrafluoroethylene and sulfonyl fluoride vinyl ether) is provided by differences in the resistance $R_F$ and capacitance $C_F$ upon exposure of the solid polymer electrolyte film coating the RFID sensor antenna structure to different vapors. See Potyrailo et al., *Analytical Chemistry* 79: 45-51, 2007, which is incorporated herein by reference. The RFID tags can convey a unique electronic code via the miniature antenna in response to a radio signal from an RFID reader, which can read the code. The code can be used to provide metadata identifying the person or garment or gloves bearing the RFID tags. The electronic code can be sent via the intranet, internet, or other means, to a server containing information relating electronic codes with specific individuals or with multilayer material garments or gloves. The detector can return the information to a microprocessor or other device. An RFID reader can also read a unique ID code from a smart tag or other device associated with the individual or the RFID sensor or both, and the code or codes can be sent to the data allocation and processing module.

An RFID detector including, in part, one or more RFID tags configured as a sensor can identify and quantify multiple gas-phase chemical compounds from a multilayer material released into an environment with a lower sensitivity limit of parts per billion. See, e.g., Potyrailo et al., Ibid. The detector can include an RFID reader (available from SkyeTek, Westminster, Colo.) and a network analyzer (Agilent Technologies, Inc., Santa Clara, Calif.) under computer control to identify and quantify analyte gases. Data on detection, identification and quantification of gas-phase chemical compounds released into the environment can be communicated by a computer to the medical glove user and healthcare team members to alert everyone a breach in the multilayer material of the glove or clothing has occurred. The RFID detector is configured to detect and quantify gas-phase chemical compounds released into an environment. The RFID detector can be incorporated in a layer of the multilayer material of the gloves and distal to the possible breach site. For example, multilayer material for a glove can be fabricated with an electronic microchip and a sensor embedded in the cuff area. See, e.g., U.S. Pat. No. 6,850,162 B2 entitled "Communicative Glove Containing Embedded Microchip" issued to Cacioli et al. on Feb. 1, 2005 which is incorporated herein by reference. The detector, including an RFID reader located proximally to one or more RFID tags configured as a sensor, can be in communication with a network analyzer and computer to detect and quantify any gas-phase chemical compounds released from a signal layer following breach of the multilayer material of the gloves. The RFID detector can also identify the individual wearing the gloves, the date and the time of the breach event. This information can be communicated to the computer and stored for future reference.

Detectors can be based on a silicon substrate incorporating a gas-sensing layer. The gas sensing layer of the detector can include a dopant including one or more of Li, Na, K, Rb, Cs, Mg, Ca, Sr, Ba, V, Cu, Zr, Hf, Al, Si, P, Tb, Ti, Mn, Fe, Co, Ni, Zn, Y, Nb, Mo, Ru, Rh, Pd, La, Ta, W, Ga, In, Sb, Bi, Ce, Sm, Gd, Cd, Re, Pt, Ge, Cr, Pb, Lu, Nd, Pr, Eu, and combinations thereof. The gas sensing layer of the detector is configured to detect at least one gas analyte including, but not limited to, NO, $NO_2$, $SO_x$, $O_2$, $H_2O$, $NH_3$, CO, $CO_2$, mercaptan, 1-hexanol, sulfur hexafluoride, ethanethiol, furaneol, or an isotopically-labeled compound, or combinations thereof. The detector can include at least one electrode of a material including, but not limited to, Pt, Au, Ag, Ni, Ti, In, Sn, Cr, nickel oxide, titanium nitride, aluminum doped zinc oxide, indium tin oxide, or a combination thereof. See, e.g., U.S. patent application numbers 2009/0159447; U.S. 2009/0159446; U.S. 2009/0159445, each of which are incorporated herein by reference.

Gas-phase chemical compound, e.g., carbon dioxide, can be detected and quantified by using a detector, e.g., a nondispersive infrared (NDIR) detector (available from Alphasense, Great Notley, Essex CM77 7AA, United Kingdom). The NDIR detector can detect gas-phase $CO_2$ at concentrations ranging from 0 to 5000 parts per million (ppm) with linearity/accuracy of ±50 ppm and a response time of less than 40 seconds at an ambient temperature of 20° C. The NDIR detector can be connected to a transmitter board with a universal serial bus (USB) output that captures data from the detector. See, e.g., "IRC-Al Carbon Dioxide Infrared Sensor" and "IRC-TM NDIR $CO_2$ Transmitter PCB" available from Alphasense, Great Notley, Essex CM77 7AA, United Kingdom which are incorporated herein by reference.

Gas-phase chemical compound, e.g., 1-hexanol, emitted from solutions of chemical compound, 1-hexanol in water, at a concentration of less than or equal to 0.01% (volume/volume) can be detected by a mass spectrometer as a detector. See, e.g., Buhr et al., *International Journal of Mass Spectrometry*, 221, 1-7, 2002 which is incorporated herein by reference. Gas-phase chemical compound, e.g., 1-hexanol, released from at least one signaling layer into an environment, can be drawn into a proton transfer reaction-mass spectrometer (PTR-MS) (available from Ionicon Analytik, Innsbruck, Austria) at 15 mL/min. Transmission of the ions through a quadruple detector can be evaluated according to the specifications of the instrument. For example, a Standard PTR-MS allows sensitive, real time detection of volatile organic chemicals. See, e.g., Ionicon Analytik GMBH, Austria. The lower limit of detection of gas-phase chemical compound, 1-hexanol, can be approximately 30 parts per trillion volumes (pptv); the linear range can be from about 30 parts per trillion volumes to about 10 parts per million volumes. The response time can be approximately 100 milliseconds. See PTR-MS Product Factsheets: *Standard PTR-MS* available from Ionicon Analytik, Innsbruck, Austria; Lindinger et al., *Advances in Gas-Phase Ion Chemistry*, 4, 1-35, 2001, each of which are incorporated herein by reference.

A system including the multilayer material including a detector can include an embedded detector. The multilayer material for medical or clean room gloves can be fabricated with a detector embedded in the multilayer material. For example, sulfur hexafluoride is a gas-phase chemical compound incorporated into the at least one signaling layer of the multilayer material that can be detected by an embedded detector. The detector can include a sensor to detect and quantify gas-phase chemical compound, sulfur hexafluoride, released into the environment following breach of the medical or clean room glove. The detector can be incorporated in a layer of the multilayer material for medical or clean room gloves. The detector can be configured to detect and quantify signal chemicals that move by convection or diffusion to an area remote from the breach site. See, e.g., U.S. Pat. No. 6,850,162 B2 entitled "Communicative Glove Containing Embedded Microchip" issued to Cacioli et al. on Feb. 1, 2005 which is incorporated herein by reference. A detector capable of identifying and quantitating multiple chemicals in the air with a lower sensitivity limit of parts per billion, integrated with an RFID device, is described by Potyrailo et al., *Analytical Chemistry* 79: 45-51, 2007, which is incorporated herein by reference. The RFID detector can include one or more RFID tags configured as a sensor and an RFID reader (available from SkyeTek, Westminster, Colo.) and a network analyzer (Agilent Technologies, Inc., Santa Clara, Calif.) under computer control that identify and quantify analyte gases with a lower limit sensitivity of 600 parts per billion. The RFID detector can also include a power supply, for example, a micro-battery that provides power to the RFID sensor and to a microprocessor that transmits wireless signals to a computer.

Data on the detection, identification and quantification of gas-phase sulfur hexafluoride signal compound following breach of a protective, or impermeable or semi-permeable, barrier layer can be sent from the detector and received and communicated by a computer to alert the glove user and other team members that a breach in the multilayer material of the glove has occurred. The detector can also include a RFID tag configured as a sensor that indicates the identity of the individual wearing the gloves, the date and the time of the breach event. This information can be received by a RFID reader and can be communicated to the computer and stored for future reference. The detector including a power supply can be attached to the gloves at the time they are first put on. Activation of the detector can initiate air monitoring and establish baseline levels (typically about 6.5 parts per trillion volumes in the air) of sulfur hexafluoride in the room or laboratory. Baseline data can be transferred to the computer where it is stored for future reference and later compared to data to remotely indicate a breach of the multilayer material.

A multilayer material can include a flexible inner layer and a flexible outer layer and at least one signaling layer containing a chemical compound, e.g., gas-phase chemical compounds, ethanethiol and/or furaneol. The detector can detect and quantify gas-phase chemical compounds from ethanethiol, and/or furaneol released into the environment following breach of the multilayer material of the medical glove.

Multilayer Material Including Environmental Detectors to Improve Detection Sensitivity of a Gas-Phase Chemical Compound By measuring environmental parameters, one can correct for undesired signals, e.g., due to humidity and temperature changes, from the detector, and thus be more sensitive to the signal from the gas-phase chemical compound. A number of approaches can be used to increase the sensitivity and selectivity of the detector and therefore decrease the amount of the gas-phase chemical compound that must be released for reliable detection of a breach in the multilayer material. Methods to increase the sensitivity and selectivity of the detector include, but are not limited to, local environmental sensing at the detector, wider-scale environmental sensing, use of isotopes of gas-phase chemical compounds, improved background sensing, improved ventilation, use of gas-phase chemical compounds that concentrate at floor or ceiling. The system including the multilayer material can include detectors that can measure environmental parameters including, but not limited to, temperature, gas and humidity resistive/capacitive detectors on flexible substrates produced from organic materials. The detector can provide temperature and gas detection in a low power demand device.

The detectors can simultaneous measure temperature, humidity and gas/vapor concentrations within one sensor platform to monitor one or more gas-phase chemical compounds released from a multilayer material into an environment to indicate a breach of the multilayer material. The differential structure of the capacitive detector system allows manufacturing of gas sensors on humidity sensitive substrate. In both polyetherurethane (PEUT)-based and polydimethylsilane (PDMS)-based detectors, one can identify specific responses towards target analyte gases from background signals due to ambient humidity. This is possible even if the background responses induced by humidity exceed by more than an order of magnitude the responses generated by the target analyte gases. This feature can be useful when designing detectors produced on hydrophobic polymeric substrates. See, e.g., A. Oprea, et al., "Integrated temperature, humidity and gas sensors on flexible substrates for low-power applications", *Proceedings of IEEE Sensors Conference*, Atlanta, USA, Oct. 28-31, 2007, pp. 158-161, which is incorporated herein by reference.

Detectors can be integrated as multiple RFID sensors and RFID readers for monitoring one or more gas-phase chemical compounds to indicate a breach of a multilayer material. Chemical and physical detectors can be produced from flexible plastic foils and transferred to the RFID detector. Direct large scale fabrication of the RFID detectors can be based on one or more printing processes. A multi-sensor flexible plastic chip including gas, humidity and temperature sensing devices with ultra low power requirements can be integrated onto an RFID detector. The RFID detector can be combined with very low power read-out circuitry and microcontroller for data acquisition and storage. For example, the RFID detector can be integrated onto polyimide foil. See, e.g., A. Oprea, et al., "Integrated temperature, humidity and gas sensors on flexible substrates for low-power applications", *Proceedings of IEEE Sensors Conference*, Atlanta, USA, Oct. 28-31, 2007, pp. 158-161; A. Oprea, et al., "Capacitive gas sensor arrays on plastic substrates for low power and mobile applications", *Proceedings of Eurosensors 2008 Conference*, Dresden, Germany, Sep. 7-10, 2008, pp. 1431-1434, each of which are incorporated herein by reference.

Gas Sensors on Plastic Foils.

RFID detectors can be integrated directly onto flexible plastic foils. The flexibility and simplified processing of flexible plastic foils, allow for targeted production of multiple RFID detectors onto large areas of flexible plastic foils using roll to roll processing from raw material to finished product and printed electronics processing. Integrated sensors can be developed into wearable, wireless RFID tags and embedded systems.

RFID gas detectors on plastic foil can be utilized for processing flexible individual sensors or flexible multi-sensor platforms. Optical, resistive (reducing and oxidizing gases) and capacitive (humidity, VOCs) based gas sensors can be developed on plastic foils, e.g., polyimide (PI), polyethylene naphthalate (PEN), or polyethylene terephthalate (PET). Performance and reliability can be achieved for ultra-low power devices that meet the requirements of wireless application for RFID gas sensors. J. Courbat, et al., "Thermal simulation and characterization for the design of ultra low power microhotplates on flexible substrate", *Proceedings of IEEE Sensors Conference*, Lecce, Italy, Oct. 26-29 2008, pp. 74-77; A. Oprea, et al., "Capacitive gas sensor arrays on plastic substrates for low power and mobile applications", *Proceedings of Eurosensors 2008 Conference*, Dresden, Germany, Sep. 7-10, 2008, pp. 1431-1434; J. Courbat, et al., "Evaluation of pH indicator-based colorimetric films for ammonia detection using optical waveguides", *Sensors and Actuators B: Chemical*, 2009, pp. 62-70; A. Oprea, et al., "Integrated temperature, humidity and gas sensors on flexible substrates for low-power applications", *Proceedings of IEEE Sensors Conference*, Atlanta, USA, Oct. 28-31, 2007, pp. 158-161; D. Briand, et al., "Integration of MOX gas sensors on polyimide hotplates", *Sensors and Actuators*, B130 (2008) 430-435; D. Briand, et al., Micro-hotplates on polyimide for sensors and actuators, *Sensors and Actuators*, A132 (2006), 317-324, each of which are incorporated herein by reference.

PROPHETIC EXAMPLES

Example 1

A medical glove that releases a gas-phase chemical compound when the glove is breached has a detector able to detect the gas-phase chemical compound and a computing device to receive, communicate and store data of the breach event.

A medical glove is manufactured using multilayer material including a flexible inner layer and a flexible outer layer configured to enclose signaling layers that produce a gas-phase chemical compound signal chemical, e.g., carbon dioxide, that signal a breach as a result of a tear, puncture, abrasion or defect in manufacture of the glove. The multilayer medical gloves are constructed from latex by using molds or by dipping or spraying hand forms. Multiple layers of latex are added in a multi-dipping manufacturing process described in U.S. Pat. No. 5,549,924 entitled "Method of Forming A Membrane, Especially A Latex or Polymer Membrane, Including A Deactivating Barrier and Indicating Layer" issued to Shlenker et al. on Aug. 27, 1996, which is incorporated herein by reference. A glove former is dipped into a coagulant solution such as calcium carbonate plus nitrate in alcohol, and then into a latex liquid. The glove former with a first latex layer is leached with water, and dried, and then the process is repeated to add additional layers of latex. Alternative methods for making multilayer membranes and multilayer gloves are described in U.S. Pat. No. 5,335,373 entitled "Protective Medical Gloves and Methods for Their Use" issued to Dangman et al. on Aug. 9, 1994, which is incorporated herein by reference.

The medical glove includes additional flexible outer layers including a protective, or impermeable or semi-permeable, barrier layer comprised of latex or a synthetic polymer, for example, poly(trans-2-chloro-1,3-butadiene), commonly known as poly(chloroprene) (available from DuPont Performance Elastomers L.L.C., Wilmington, Del. 19809). The protective barrier layer and other outer layers can be reinforced by adding microfibers to the polymer or latex solutions prior to dipping or spraying the glove formers. Microfibers for reinforcement include aramids, Kevlar, fiber glass, and nylon. A signal chemical, e.g., carbon dioxide in a gaseous phase, can be released from a flexible inner layer of the medical glove and thereby signal when the glove is breached. One or more additional signaling layers of latex or polymer is applied to enclose and contain the chemical compounds. The multilayer medical glove contains different chemicals in different signaling layers that react to form the gas-phase chemical compound. To produce gas-phase carbon dioxide, a first signaling layer contains aqueous 0.8 moles/liter (M) sodium bicarbonate ($NaHCO_3$) and an adjacent signaling layer contains aqueous 0.26 M citric acid ($C_6H_8O_7$) external to the first signaling layer. The glove can be breached by puncturing an external flexible outer layer and the signaling layers of the multilayer medical glove. The breach of the multilayer material results in mixing of sodium bicarbonate and citric acid in the signaling layers which react to form gas-phase carbon dioxide ($CO_2$). The chemical reaction is:

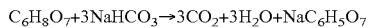
$$C_6H_8O_7 + 3NaHCO_3 \rightarrow 3CO_2 + 3H_2O + NaC_6H_5O_7$$

Gas-phase compound, $CO_2$, is released into the air from a breach of the multilayer material and is detected by a detector. Carbon dioxide is detected and quantified by using a nondispersive infrared (NDIR) sensor (available from Alphasense, Great Notley, Essex CM77 7AA, United Kingdom). Multiple NDIR sensors are located on the walls and ceiling of the room where the medical gloves are being used. The NDIR sensor detects gas-phase $CO_2$ at concentrations ranging from 0 to 5000 parts per million (ppm) with linearity/accuracy of ±50 ppm and a response time of less than 40 seconds at an ambient temperature of 20° C. The NDIR sensor is connected to a transmitter board with a universal serial bus (USB) output that captures data from the sensor. See the Technical Specification sheets: "IRC-A1 Carbon Dioxide Infrared Sensor" and "IRC-TM NDIR $CO_2$ Transmitter PCB" available from Alphasense, Great Notley, Essex CM77 7AA, United Kingdom which are incorporated herein by reference. The data from the NDIR sensor can be stored for later download to a computer or can be connected by wire or wirelessly to a computer. A continuous record of ambient $CO_2$ levels, times and dates are stored in the computer corresponding to NDIR sensors for $CO_2$ placed in multiple hospital rooms, surgery suites, emergency rooms and intensive care units. Ambient levels of $CO_2$ are monitored continuously to establish a baseline level of $CO_2$ for each room. Carbon dioxide released into the air following breach of a glove is detected after diffusion of the gas into the NDIR sensor/transmitter and the time, date and amount of $CO_2$ (in ppm) is acquired and stored by a computer. A significant increase of $CO_2$ concentration above baseline level (indoor air typically contains 600-1000 ppm $CO_2$) triggers an alert. If a $CO_2$ concentration significantly (e.g., greater than 1000 ppm) above the baseline level for the room is detected the computer communicates an alert that a glove breach may have occurred. The computer triggers an audio alert through its speakers or a flashing alert on a user-interface display to alert the individuals in the room and other healthcare workers and safety officials to promote containment of any infectious agents.

Example 2

A multilayer medical glove that releases a chemical compound to indicate a breach of the glove has a detector able to detect a gas-phase chemical compound and alert healthcare workers that a breach has occurred.

Multilayer gloves are manufactured using a multilayer material including a flexible inner layer and a flexible outer layer configured to enclose a signaling layer that will release a gas-phase chemical compound, e.g., 1-hexanol, when the multilayer glove is breached, and a gas detector communicating to a transmitter and to a computer system programmed to alert a wearer that a breach has occurred and prompts immediate action.

The multilayer medical gloves are constructed from latex, polyurethane, polyethylene, rubber and other elastomers and polymers by using molds or by dipping or spraying forms. For example, multiple layers of latex are added in a multi-dipping manufacturing process described in U.S. Pat. No. 5,549,924 entitled "Method of Forming A Membrane, Especially A Latex or Polymer Membrane, Including A Deactivating Barrier and Indicating Layer" issued to Shlenker et al. on Aug. 27, 1996 which is incorporated herein by reference. A glove former is dipped into a coagulant solution such as calcium carbonate plus nitrate in alcohol, and then into a latex liquid. The glove former with a first latex inner layer is leached with water, and dried, and then the process is repeated to add additional inner layers of latex. Alternative methods for making multilayer membranes and multilayer gloves are described in U.S. Pat. No. 5,335,373 entitled "Protective Medical Gloves and Methods for Their Use" issued to Dangman et al. on Aug. 9, 1994, which is incorporated herein by reference. The medical glove has flexible outer layers including a protective barrier layer comprised of latex or a synthetic polymer, for example, poly(trans-2-chloro-1,3-butadiene), commonly known as poly(chloroprene) (available from DuPont Performance Elastomers L.L.C., Wilmington, Del. 19809). 1-hexanol, a gas-phase chemical compound signal chemical, is incorporated within multiple signaling layers of the medical glove to signal breach of the multilayer material of the glove. 1-hexanol is available from Sigma-Aldrich, St. Louis, Mo. Gas-phase signal chemicals, e.g., 1-hexanol, and indicator dyes are incorporated within and between the layers of multilayer gloves by mixing the chemicals with latex or polymer liquids prior to dipping the glove formers and adding the next layer. For example, methods for making multilayer membranes with indicator dyes, crystals, colored agents or congealing substances are given in U.S. Pat. No. 5,549,924 entitled "Method of Forming A Membrane, Especially A Latex or Polymer Membrane, Including A Deactivating Barrier and Indicating Layer" issued to Shlenker et al. on Aug. 27, 1996 which is incorporated herein by reference. One or more additional layers of latex or polymer are applied to enclose and contain the chemical compounds.

The multilayer gloves contain a chemical compound, 1-hexanol, a volatile compound that is released upon breach of the multilayer material. Gas-phase 1-hexanol is emitted from solutions of 1-hexanol in water incorporated within the at least one signaling layer of the multilayer glove. Gas-phase 1-hexanol emitted from solutions of 1-hexanol in water at a concentration of less than or equal to 0.01% (volume/volume) are detectable by mass spectrometry (see Buhr et al., *International Journal of Mass Spectrometry*, 221, 1-7, 2002, which is incorporated herein by reference).

Air containing 1-hexanol is drawn into a proton transfer reaction-mass spectrometer (PTR-MS) (available from Ionicon Analytik, Innsbruck, Austria) at 15 mL/min and transmission of the ions through a quadruple detector is evaluated according to the specifications of the instrument. For example, a Standard PTR-MS from Ionicon Analytik allows sensitive, real time detection of volatile organic chemicals. The lower limit of detection is 30 parts per trillion volumes (pptv); linear range is 30 pptv-10 parts per million volumes. The response time is approximately 100 milliseconds. See PTR-MS Product Factsheets: *Standard PTR-MS* available from Ionicon Analytik, Innsbruck, Austria and Lindinger et al., *Advances in Gas-Phase Ion Chemistry*, 4, 1-35, 2001, which are incorporated herein by reference.

The PTR-MS detects the release of 1-hexanol from the glove breach into the hospital room air and communicates with a computer to which it is hardwired that is programmed to alert all individuals in the room that a breach of a glove has occurred. A preset criterion for the minimum concentration of 1-hexanol to trigger an alert is established to discriminate background levels of 1-hexanol that may be present in the air. Also the computer is suitably programmed to alert health and safety officials remotely that a breach of medical gloves has occurred, the location (room) of the breach event and the time of the breach event. Moreover, all data concerning the breach event are stored on the computer for later reference.

Example 3

Gloves for handling hazardous materials release a chemical compound from the multilayer material of the gloves when the gloves are breached and the gas-phase chemical compound is detected with a detector located on the gloves.

Examination gloves for handling hazardous materials are manufactured using a multilayer material including a flexible inner layer and a flexible outer layer configured to enclose multiple signaling layers that releases a gas-phase chemical compound, sulfur hexafluoride, which is detectable when the gloves are breached as a result of a puncture or tear in the glove material. A powered detector chip located on the gloves detects the gas-phase chemical compound released from the area of puncture or tear in the gloves. The powered detector chip transmits data to a computer via a transmitter to indicate that a breach in the gloves has occurred. The computer is suitably programmed to immediately alert everyone in the area as well as remote notification of health and safety officers that a breach has occurred. The examination glove is comprised of multiple signaling layers of latex containing a gas-phase chemical compound, sulfur hexafluoride, which is released into the air when the glove is breached.

The glove contains a detector chip embedded in the cuff of the glove. The detector chip includes a radio-frequency identification (RFID) sensor that detects sulfur hexafluoride and a microprocessor that relays a wireless signal to a computer indicating the amount of sulfur hexafluoride detected. The computer is suitably programmed to provide a record of the amount of sulfur hexafluoride detected, and the date and time sulfur hexafluoride is detected, and alerts the individual wearing the glove, as well as coworkers and health and safety officials that a glove breach has occurred.

The examination glove is constructed of multiple layers including a flexible inner layer and a flexible outer layer configured to enclose at least one signaling layer containing chemicals that signal a breach (e.g., a tear, puncture, abrasion or defect in manufacture) of the glove. Multilayer examination gloves used in industrial laboratories, bioprocessing plants, research laboratories, biosafety level two and biosafety level three facilities hospitals, and clinics are constructed from nitrile by dipping glove forms. Multiple inner layers of nitrile are added in a multi-dipping manufacturing process described in U.S. Pat. No. 6,347,408 entitled "Powder-free Gloves Having a Coating Containing Cross-linked Polyurethane and Silicone and Method of Making the Same" issued to Yeh et al. on Feb. 19, 2002 which is incorporated herein by reference. A glove former is dipped in a coagulant dispersion comprised of calcium nitrate, calcium carbonate powders, wetting agents and water (or alcohol for alcohol based coagulant dispersion). The coagulant layer deposited on the glove former is allowed to dry. The glove former with the dried coagulant layer is then dipped into a compounded nitrile latex maintained at about 68° F. to about 86° F. The glove former with a first nitrile layer is leached with water for 3 to 10 minutes at 78-110° F. and then dried. The dipping process is repeated to add additional inner layers, signaling layers, and outer layers of nitrile. Alternative methods for making multilayer membranes and multilayer gloves are described in U.S. Pat. No. 5,335,373 entitled "Protective Medical Gloves and Methods for Their Use" issued to Dangman et al. on Aug. 9, 1994, which is incorporated herein by reference. The medical glove has a protective barrier layer comprised of a synthetic polymer, for example, poly(trans-2-chloro-1,3-butadiene), commonly known as poly(chloroprene) (available from DuPont Performance Elastomers L.L.C., Wilmington, Del. 19809).

The examination glove includes a gas-phase chemical compound signal chemical, sulfur hexafluoride. Sulfur hexafluoride gas (available from Concorde Specialty Gases, Inc., Eatontown, N.J. 07724) is added between two signaling layers of the multilayer glove by inflating the space at low pressure between the adjacent signaling layers. After infusion of sulfur hexafluoride gas, the gas inlet on the glove is sealed. Methods to construct gloves with a sealable gas inlet are described in U.S. Pat. No. 5,911,848 entitled "Method for Making A Puncture Evident Double Layer Surgical Glove" issued to Haber et al. on Jun. 15, 1999, which is incorporated herein by reference. Multilayer gloves with a sealed reservoir between two layers are described in U.S. Pat. No. 5,549,924 entitled "Method of Forming A Membrane, Especially A Latex or Polymer Membrane, Including A Deactivating Barrier and Indicating Layer" issued to Shlenker et al. on Aug. 27, 1996, which is incorporated herein by reference.

The examination glove is fabricated with an RFID detector embedded in the glove. The RFID detector includes an RFID sensor to detect and quantify gas-phase sulfur hexafluoride released into the environment following breach of the glove. The RFID detector is incorporated in one or more outer layers of the medical gloves to detect and quantify signal chemicals. The RFID detector is remote from the potential breach site. For example, a glove is fabricated with an electronic microchip embedded in the cuff area. See, e.g., U.S. Pat. No. 6,850,162 B2 entitled "Communicative Glove Containing Embedded Microchip" issued to Cacioli et al. on Feb. 1, 2005; U.S. Pat. No. 6,060,986, "Protective glove breach monitoring"; U.S. Pat. No. 5,734,323, "Puncture detecting barrier materials"; each of which are incorporated herein by reference. The RFID sensor is capable of identifying and quantitating multiple chemicals in the air with a lower sensitivity limit of parts per billion. See, e.g., Potyrailo et al., *Analytical Chemistry* 79: 45-51, 2007, which is incorporated herein by reference. The RFID detector includes an RFID sensor and an RFID reader (available from SkyeTek, Westminster, Colo.) and a network analyzer (Agilent Technologies, Inc., Santa Clara, Calif.) under computer control to identify and quantify analyte gases with a lower limit sensitivity of 600 parts per billion. The detector chip also includes a power supply, for example, a micro-battery that provides power to the RFID sensor and to a microprocessor that transmits wireless signals to a computer.

Data on the detection, identification and quantification of gas-phase sulfur hexafluoride signal compound is sent from the RFID sensor and RFID reader in the RFID detector and received and communicated via a transmitter to a computer to alert the glove user and other team members that a breach in the glove has occurred. The RFID detector also includes an RFID tag indicating the identity of the individual wearing the gloves, the date and the time of the breach event. This information is communicated to the computer and stored for future reference. The RFID detector including a power supply is attached to the gloves at the time they are first put on. Activation of the detector chip initiates air monitoring and establishes baseline levels (typically about 6.5 parts per trillion volumes in the air) of sulfur hexafluoride in the room or laboratory. Baseline data is transferred to the computer where it is stored for future reference. The gloves are disposable and the detector chip is transferred to a new pair of gloves.

Example 4

A medical glove that releases chemical compounds when the glove is breached and a detector to detect the gas-phase chemical compounds and a computing device to receive, communicate and store data from the breach event.

A medical glove is constructed from a multilayer material including a flexible inner layer and a flexible outer layer configured to enclose multiple signaling layers that contains gas-phase chemical compounds, e.g., ethanethiol and furaneol, that signal a breach of the glove, such as a tear, puncture, abrasion or defect in manufacture of the glove. Multilayer medical gloves used by physicians, nurses and other healthcare workers are constructed from polyurethane by dipping forms. Multiple inner layers of polyurethane are added in a multi-dipping manufacturing process described in U.S. Pat. No. 5,549,924 entitled "Method of Forming A Membrane, Especially A Latex or Polymer Membrane, Including A Deactivating Barrier and Indicating Layer" issued to Shlenker et al. on Aug. 27, 1996 and in U.S. Pat. No. 6,347,408 entitled "Powder-free Gloves Having a Coating Containing Crosslinked Polyurethane and Silicone and Method of Making the Same" issued to Yeh et al. on Feb. 19, 2002 which are incorporated herein by reference. A glove former is dipped into a coagulant solution such as calcium carbonate plus nitrate in alcohol, and then into a polyurethane dispersion. The process is repeated to add additional inner layers, signaling layers, and outer layers of polyurethane or other polymers. Alternative methods for making multilayer membranes and multilayer gloves are described in U.S. Pat. No. 5,335,373 entitled "Protective Medical Gloves and Methods for Their Use" issued to Dangman et al. on Aug. 9, 1994, which is incorporated herein by reference. The medical gloves have an outer layer as a protective barrier layer comprised of latex or a synthetic polymer, for example, poly(trans-2-chloro-1,3-butadiene), commonly known as poly(chloroprene) (available from DuPont Performance Elastomers L.L.C., Wilmington, Del. 19809).

Ethanethiol, in combination with furaneol, are incorporated within multiple signaling layers of the medical glove to signal when released from a puncture or tear in the glove. Ethanethiol and furaneol are available from Sigma-Aldrich, St. Louis, Mo. Signal chemicals and indicator dyes are incorporated within and between the signaling layers of multilayer gloves by mixing the chemicals with polymer liquids prior to dipping the glove formers and adding the next layer. See, e.g., U.S. Pat. No. 5,549,924 entitled "Method of Forming A Membrane, Especially A Latex or Polymer Membrane, Including A Deactivating Barrier and Indicating Layer" issued to Shlenker et al. on Aug. 27, 1996, which is incorporated herein by reference. One or more additional signaling layers of polyurethane polymer are applied to enclose and contain the chemical compounds. The multilayer medical glove contains multiple signal chemicals in different signaling layers that are internal or external to the one or more outer protective barrier layers. One or more signaling layers interior to the protective barrier layer contains ethanethiol, and one or more signaling layers external to the protective barrier layer contains furaneol. Release of gas-phase ethanethiol signals breach of the protective barrier layer, and release of gas-phase furaneol signals breach of a layer external to the protective barrier layer.

The glove system also includes a radio-frequency identification (RFID) detector including an RFID sensor and an RFID reader attached to the glove. The RFID sensor detects and quantifies gas-phase chemical compounds, ethanethiol, furaneol, or an isotopically-labeled compound, released into the air following breach of one or more protective barrier layers or external layers of the medical glove. An RFID detector capable of identifying and quantitating multiple chemicals in the air with a lower sensitivity limit of parts per billion is described by Potyrailo et al., *Analytical Chemistry* 79: 45-51, 2007, which is incorporated herein by reference. The RFID detector includes an RFID sensor and an RFID reader (available from SkyeTek, Westminster, Colo.) and a network analyzer (Agilent Technologies, Inc., Santa Clara, Calif.) under computer control to identify and quantify analyte gases at a lower limit sensitivity of 600 parts per billion. The detector chip also includes a power supply, for example, a microbattery that provides power to the RFID sensor and to a microprocessor that transmits wireless signals to a computer. Data on detection, identification and quantification of signal chemicals is received and communicated via a transmitter to a computer to alert the glove user and other team members that a breach in the glove has occurred. The computer is programmed to alert the medical glove user and healthcare team members that a breach in the medical glove has occurred. The RFID sensor is incorporated in one or more layers of the multilayer material of the medical gloves to detect and quantify signal chemicals. The RFID detector is remote from the potential breach site. For example, a glove is fabricated with an electronic microchip embedded in the cuff area. See, e.g., U.S. Pat. No. 6,850,162 B2 entitled "Communicative Glove Containing Embedded Microchip" issued to Cacioli et al. on Feb. 1, 2005; U.S. Pat. No. 6,060,986, "Protective glove breach monitoring"; U.S. Pat. No. 5,734,323, "Puncture detecting barrier materials"; each of which are incorporated herein by reference. An RFID detector includes an RFID reader located proximally to the RFID sensor and connected wirelessly to a network analyzer and computer to detect and quantify any signal chemicals released following breach of the gloves. The RFID detector also includes an RFID tag indicating the identity of the individual wearing the gloves, the date and the time of the breach event and this information is communicated to the computer and stored for future reference.

Example 5

A protective garment that releases a chemical compound, a signal detector that detects a gas-phase chemical compound and a computer to alert the wearer and other key personnel that the garment has been breached.

A protective laboratory suit is constructed from a multilayer material including a flexible inner layer and a flexible outer layer configured to enclose a signaling layer that contains a gas-phase chemical compound, ethanethiol. The suit also is equipped with a radio-frequency identification (RFID) detector that detects ethanethiol and signals that a breach, such as a tear, puncture, abrasion or defect in manufacture, of the laboratory suit may have occurred. Following a puncture, the multilayer material of the protective suit releases gas-phase ethanethiol from a signaling layer of the suit into the air and the ethanethiol gas is detected by a RFID detector that is part of the garment. The RFID detector includes an RFID sensor that communicates with a RFID reader and transmitter and in turn, a wirelessly linked suitably programmed computer to evaluate whether a breach event has occurred. If the concentration (parts per billion volumes) of ethanethiol significantly exceeds baseline levels (determined by the RFID detector) the computer is programmed to alert the user wearing the suit and/or health and safety authorities that a breach of the protective suit may have occurred.

A protective laboratory suit including a hat, face mask, long sleeved shirt, pants and booties is constructed of a multilayer fabric/membrane that is comprised of synthetic polymers. For example methods and compositions to make a multilayer fabric from a layer of polypropylene that is laminated with a polyethylene film is described in U.S. Pat. No. 7,225,476 entitled "Protective Clothing Against Biological Agents" issued to Cerbini and Lo loco on Jun. 5, 2007 which is incorporated herein by reference. The signal chemical, ethanethiol, is incorporated within a signaling layer of the multilayer material of the protective fabric to signal breach of the protective suit. Signal chemicals, ethanethiol, are incorporated within and between the signaling layer of the multilayer material by mixing the chemicals with latex or polymer liquids prior to forming (i.e., polymerizing or vulcanizing) a layer of the multilayer material of the protective fabric. See, e.g., U.S. Pat. No. 5,549,924 entitled "Method of Forming A Membrane, Especially A Latex or Polymer Membrane, Including A Deactivating Barrier and Indicating Layer" issued to Shlenker et al. on Aug. 27, 1996, which is incorporated herein by reference. One or more additional signaling layers of polymer are applied to enclose and contain the ethanethiol chemical compound in the signaling layer. A solution of 18 moles/liter (M) ethanethiol is diluted ten-fold into a liquid polymer (e.g., polypropylene) and incorporated in a multilayer material. Alternatively, a solution of 1.8 M ethanethiol is injected into a multilayer fabric with a void space between the signaling layers. See, e.g., U.S. Pat. No. 5,549,924 entitled "Method of Forming A Membrane, Especially A Latex or Polymer Membrane, Including A Deactivating Barrier and Indicating Layer" issued to Shlenker et al. on Aug. 27, 1996, which is incorporated herein by reference.

The protective suit is fabricated with a detector embedded in the sleeve. The detector includes an RFID sensor and an RFID reader. The RFID sensor detects and quantifies the gas-phase ethanethiol chemical compound released from a layer of the suit into the environment following breach of one or more layers of the multilayer material of the protective suit. The RFID detector is incorporated in the protective suit to detect and quantify gas-phase ethanethiol signal chemical. The RFID detector is remote from the potential breach site. See, e.g., U.S. Pat. No. 6,850,162 B2 entitled "Communicative Glove Containing Embedded Microchip" issued to Cacioli et al. on Feb. 1, 2005 which is incorporated herein by reference. The RFID sensor is capable of identifying and quantitating multiple chemicals in the air with a lower sensitivity limit of parts per billion. See, e.g., Potyrailo et al., *Analytical Chemistry* 79: 45-51, 2007, which is incorporated herein by reference. The RFID detector includes an RFID sensor and a powered RFID reader (available from SkyeTek, Westminster, Colo.) and a network analyzer (Agilent Technologies, Inc., Santa Clara, Calif.) under computer control programmed to identify and quantify gas-phase ethanethiol with a lower limit sensitivity range of 50-600 parts per billion. The detector chip also contains a power supply including a micro-battery that provides power to the RFID sensor and to a microprocessor that transmits wireless signals to a computer.

Data on the detection, identification and quantification of gas-phase ethanethiol signal chemical are sent from the RFID sensor and RFID reader in the RFID detector to a transmitter and is received and communicated by a computer to alert the protective suit user and other team members that a breach in the protective suit has occurred. The RFID detector also includes a RFID tag indicating the identity of the individual wearing the protective suit, the date and the time of the breach event. This information is communicated to the computer and stored for future reference. The RFID detector including a power supply is attached to the protective suit at the time it is put on, and the detector chip is removed and reused with freshly sterilized suits or new suits. Activation of the detector chip by installation in a protective suit initiates air monitoring to establish baseline levels of ethanethiol in the room or laboratory and baseline data is transferred to a computer where it is stored for future reference.

Each disclosed range of values of dosages or stimulus signal includes all combinations and sub-combinations of range values, as well as specific numerals contained therein.

All publications and patent applications cited in this specification are herein incorporated by reference to the extent not inconsistent with the description herein and for all purposes as if each individual publication, patent or patent application were specifically and individually indicated to be incorporated by reference for all purposes.

The state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Optical aspects of implementations will typically employ optically-oriented hardware, software, and or firmware.

In a general sense the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

The herein described components (e.g., steps), devices, and objects and the description accompanying them are used as examples for the sake of conceptual clarity and that various configuration modifications using the disclosure provided herein are within the skill of those in the art. Consequently, as used herein, the specific examples set forth and the accompanying description are intended to be representative of their more general classes. In general, use of any specific example herein is also intended to be representative of its class, and the non-inclusion of such specific components (e.g., steps), devices, and objects herein should not be taken as indicating that limitation is desired.

With respect to the use of substantially any plural or singular terms herein, the reader can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable or physically interacting components or wirelessly interactable or wirelessly interacting components or logically interacting or logically interactable components.

While particular aspects of the present subject matter described herein have been shown and described, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an"; the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art after reading the disclosure herein. The various aspects and embodiments disclosed herein are for purposes of illustration and are not intended to be limiting, with the true scope and spirit being indicated by the following claims.

What is claimed is:

1. A multilayer material comprising:
   a flexible inner layer and a flexible outer layer configured to enclose at least one signaling layer including at least one chemical compound; wherein the flexible outer layer is substantially impermeable to an environment and to the at least one chemical compound in the at least one signaling layer; and wherein the at least one chemical compound within the at least one signaling layer is configured to produce at least one gas-phase chemical compound configured to be released into the environment upon exposure of the at least one chemical compound to the environment.

2. The multilayer material of claim 1, further including a detector configured to detect the at least one gas-phase chemical compound or a reaction product thereof in the environment indicating a breach of the multilayer material.

3. The multilayer material of claim 2, wherein the detector is configured to form a layer of the multilayer material.

4. The multilayer material of claim 2, wherein the detector is configured to operate in contact with the multilayer material.

5. The multilayer material of claim 2, wherein the detector is configured to measure one or more absolute levels of the at least one gas-phase chemical compound or the reaction product thereof.

6. The multilayer material of claim 2, wherein the detector is configured to measure one or more comparisons between the one or more absolute levels and one or more baseline levels of the at least one gas-phase chemical compound or the reaction product thereof.

7. The multilayer material of claim 2, wherein the detector is configured to measure the rate of change of concentration of the at least one gas-phase chemical compound or the reaction product thereof.

8. The multilayer material of claim 2, wherein the detector is configured to identify the at least one gas-phase chemical compound or the reaction product thereof.

9. The multilayer material of claim 2, wherein the reaction product is due to a reaction of the at least one gas-phase chemical compound and the environment.

10. The multilayer material of claim 2, wherein the gas-phase chemical compound is due to a reaction of the at least one chemical compound and the environment.

11. The multilayer material of claim 1, wherein the at least one gas-phase chemical compound is substantially removed from the environment within a specified time.

12. The multilayer material of claim 2, further including a remote receiver, wherein the detector is configured to deliver a signal to the remote receiver.

13. The multilayer material of claim 12, wherein the signal includes data associated with the identity of the at least one gas-phase chemical compound, concentration of the at least one gas-phase chemical compound, comparison of concentration of the at least one gas-phase chemical compound to baseline, or ratio of concentrations of the at least one gas-phase chemical compounds.

14. The multilayer material of claim 12, wherein the signal includes data associated with the identity of the reaction product, concentration of the reaction product, comparison of concentration of the reaction product to baseline, or ratio of concentrations of the reaction products.

15. The multilayer material of claim 12, wherein the signal includes a wireless signal.

16. The multilayer material of claim 2, wherein the detector includes at least one of a radio frequency identification sensor and a radio frequency identification reader.

17. The multilayer material of claim 2, wherein the multilayer material includes at least one of a radio frequency identification sensor and a radio frequency identification reader.

18. The multilayer material of claim 1, wherein the at least one signaling layer including the at least one chemical compound includes a liquid-phase chemical compound or a solid-phase chemical compound.

19. The multilayer material of claim 1, wherein the at least one signaling layer including the at least one chemical compound includes the at least one gas-phase chemical compound.

20. The multilayer material of claim 1, wherein the at least one chemical compound is microencapsulated in the at least one signaling layer.

21. The multilayer material of claim 1, wherein the at least one chemical compound includes mercaptan, carbon dioxide, 1-hexanol, sulfur hexafluoride, ethanethiol, or furaneol.

22. The multilayer material of claim 1, wherein the at least one chemical compound includes $^{13}CO_2$, $C^{18}O^{16}O$, $D_2O$, DHO, or other isotopically-distinctive compound.

23. The multilayer material of claim 2, wherein the at least one gas-phase chemical compound is configured to be lighter or heavier than air and flow to the detector.

24. The multilayer material of claim 2, wherein the at least one gas-phase chemical compound is transferred to the detector by active convection.

25. The multilayer material of claim 12, wherein the detector is further configured to transmit metadata to the remote receiver.

26. The multilayer material of claim 25, wherein the metadata includes multilayer material identification, user identification, location of the breach in the multilayer material, detection event time, or multilayer material location.

27. The multilayer material of claim 2, wherein the detector is configured to store signal data or metadata on board the detector for future readout.

28. The multilayer material of claim 12, wherein the detector or the remote receiver is configured to communicate with a computing device.

29. The multilayer material of claim 1, wherein the multilayer material includes an article of clothing, a bandage, an enclosure, packaging, a surgical drape, a glove box, or a food wrapping.

30. The multilayer material of claim 1, wherein the at least one signaling layer includes two or more chemical compounds in a same location on the multilayer material, wherein the ratio of two or more gaseous chemical compounds derived from the two or more chemical compounds identifies the multilayer material or identifies the same location on the multilayer material.

31. The multilayer material of claim 1, wherein the at least one signaling layer includes two or more chemical compounds in two or more different locations on the multilayer material, wherein the release of one or more gaseous chemical compounds derived from at least one of the two or more chemical compounds to the environment is configured to identify at least one release location on the multilayer material.

32. The multilayer material of claim 31, wherein the two or more different locations of the two or more chemical compounds in the at least one signaling layer includes one or more of two or more different lateral locations and two or more different layered locations on the multilayer material.

33. The multilayer material of claim 31, wherein each of the two or more different locations has at least one distinct chemical compound.

34. The multilayer material of claim 31, wherein each of the two or more different locations has a distinct ratio of the two or more chemical compounds.

35. A system comprising:
a multilayer material including a flexible inner layer and a flexible outer layer configured to enclose at least one signaling layer including at least one chemical compound; wherein the flexible outer layer is substantially impermeable to an environment and to the at least one chemical compound in the at least one signaling layer; and wherein the at least one chemical compound within the at least one signaling layer is configured to produce at least one gas-phase chemical compound configured to be released into the environment upon exposure to the environment; and
a detector configured to detect the at least one gas-phase chemical compound or a reaction product thereof in the environment.

36. The system of claim 35, wherein the detector is configured to form a layer of the multilayer material.

37. The system of claim 35, wherein the detector is configured to operate in contact with the multilayer material.

38. The system of claim 35, wherein the detector is configured operate at a distance from the multilayer material.

39. The system of claim 35, comprising a device to substantially remove the at least one gas-phase chemical compound from the environment within a specified time.

40. The system of claim 39, wherein the device substantially removes the at least one gas-phase chemical compound from the environment by a chemical reaction with at least one normal component of the atmosphere.

41. The system of claim 39, wherein the device substantially removes the at least one gas-phase chemical compound from the environment by a chemical reaction with a chemical released or exposed subsequent to detection of the at least one gas-phase chemical compound.

42. The system of claim 39, wherein the device substantially removes the at least one gas-phase chemical compound from the environment by condensation.

43. The system of claim 39, wherein the device substantially removes the at least one gas-phase chemical compound from the environment by photodissociation.

44. The system of claim 39, wherein the device substantially removes the at least one gas-phase chemical compound from the environment by active convection.

45. The system of claim 44, wherein the active convection is continuous or is activated by detection of the at least one gas-phase chemical compound.

46. The system of claim 39, wherein the device substantially removes the at least one gas-phase chemical compound from the environment by passive convection.

47. The system of claim 35, further including a remote receiver, wherein the detector is configured to deliver a signal to the remote receiver.

48. The system of claim 47, wherein the signal includes data associated with the identity of the reaction product, concentration of the reaction product, comparison of concentration of the reaction product to baseline, or ratio of concentrations of the reaction products.

49. The system of claim 35, wherein the at least one chemical compound is microencapsulated in the at least one signaling layer.

50. The system of claim 47, wherein the detector or the remote receiver is configured to communicate with a computing device.

51. The system of claim 35, wherein the at least one signaling layer includes two or more chemical compounds in a same location on the multilayer material, wherein the ratio of two or more gaseous chemical compounds derived from the two or more chemical compounds identifies the multilayer material or identifies the same location on the multilayer material.

52. The system of claim 35, wherein the at least one signaling layer includes two or more chemical compounds in two or more different locations on the multilayer material, wherein the release of one or more gaseous chemical compounds derived from at least one of the two or more chemical compounds to the environment is configured to identify at least one release location on the multilayer material.

53. A system for use on a computer, comprising
a non-transient computer-readable medium including instructions for analyzing a signal to a detector indicating a breach of a multilayer material, wherein the multilayer material includes a flexible inner layer and a flexible outer layer configured to enclose a at least one signaling layer including at least one chemical compound; wherein the flexible outer layer is substantially impermeable to an environment and to the at least one chemical compound in the at least one signaling layer; and wherein the at least one chemical compound within the at least one signaling layer is configured to produce at least one gas-phase chemical compound configured to be released into the environment upon exposure of the at least one chemical compound to the environment; and a non-transient computer-readable medium including instructions for analyzing metadata provided to the detector configured to detect the at least one gas-phase chemical compound or a reaction product thereof in the environment indicating the breach of the multilayer material.

54. The system of claim 53, further including instructions for analyzing data from a remote receiver, wherein the remote receiver is configured to receive a second signal transmitted from the detector indicating the breach in the multilayer material.

* * * * *